United States Patent
Stone et al.

(10) Patent No.: US 8,535,357 B2
(45) Date of Patent: Sep. 17, 2013

(54) CONTINUOUS PHASE COMPOSITIONS FOR ACL REPAIR

(75) Inventors: Kevin T. Stone, Winona Lake, IN (US); Mark D. Borden, Collegeville, PA (US)

(73) Assignee: Biomet Sports Medicine, LLC, Warsaw, IN (US)

(*) Notice: Subject to any disclaimer, the term of this patent is extended or adjusted under 35 U.S.C. 154(b) by 1659 days.

(21) Appl. No.: 11/702,448

(22) Filed: Feb. 5, 2007

(65) Prior Publication Data

US 2007/0141110 A1 Jun. 21, 2007

Related U.S. Application Data

(63) Continuation-in-part of application No. 11/008,075, filed on Dec. 9, 2004, now Pat. No. 7,879,109.

(51) Int. Cl.
*A61B 17/04* (2006.01)
*A61B 17/84* (2006.01)
*A61F 2/08* (2006.01)
*A61F 2/00* (2006.01)
*F16B 35/06* (2006.01)

(52) U.S. Cl.
USPC ............................ 606/300; 424/426; 411/403

(58) Field of Classification Search
USPC ............. 606/76, 77, 301, 304, 314, 321, 323, 606/305, 300; 411/403, 407; 424/426
See application file for complete search history.

(56) References Cited

U.S. PATENT DOCUMENTS

| | | | |
|---|---|---|---|
| 4,349,921 A | 9/1982 | Kuntz | |
| 4,421,112 A | 12/1983 | Mains et al. | |
| 4,450,591 A | 5/1984 | Rappaport | |
| 4,516,276 A | 5/1985 | Mittelmeier et al. | |
| 4,612,923 A | 9/1986 | Kronenthal | |
| 4,655,777 A | 4/1987 | Dunn et al. | |
| 4,678,470 A | 7/1987 | Nashef et al. | |
| 4,713,076 A * | 12/1987 | Draenert ..................... 623/23.6 | |
| 4,743,256 A | 5/1988 | Brantigan | |
| 4,770,860 A | 9/1988 | Ewers et al. | |
| 4,834,754 A | 5/1989 | Shearing | |
| 4,842,603 A | 6/1989 | Draenert et al. | |
| 4,863,472 A | 9/1989 | Tormala et al. | |
| 4,878,915 A | 11/1989 | Brantigan | |
| 4,904,261 A | 2/1990 | Dove et al. | |

(Continued)

FOREIGN PATENT DOCUMENTS

| WO | WO 97/46178 | 12/1997 |
|---|---|---|
| WO | WO 97/47334 | 12/1997 |
| WO | WO 2006/015316 | 2/2006 |

OTHER PUBLICATIONS

Agrawal et al., "Technique to Control pH in Vicinty of Biodegrading PLA-PGA Implants", John Wiley & Sons, Inc. (1997) pp. 105-114.

(Continued)

*Primary Examiner* — Kevin T Truong
*Assistant Examiner* — David Bates
(74) *Attorney, Agent, or Firm* — Harness, Dickey

(57) ABSTRACT

An implantable interference screw for use in a soft tissue repair, the screw having a bioresorbable body comprising a plurality of interconnected pores, the body having an instrument interface in one end and a thread around an exterior of the body starting from distal end. The plurality of interconnected pores of the resorbable body are substantially filled with a bioresorbable polymer.

29 Claims, 10 Drawing Sheets

(56) References Cited

U.S. PATENT DOCUMENTS

| | | | |
|---|---|---|---|
| 4,976,736 A * | 12/1990 | White et al. | 424/423 |
| 5,015,255 A | 5/1991 | Kuslich | |
| 5,026,373 A | 6/1991 | Ray et al. | |
| 5,053,039 A | 10/1991 | Hofmann et al. | |
| 5,059,209 A | 10/1991 | Jones | |
| 5,192,327 A | 3/1993 | Brantigan | |
| 5,306,309 A | 4/1994 | Wagner et al. | |
| 5,338,772 A | 8/1994 | Bauer et al. | |
| 5,360,450 A | 11/1994 | Giannini | |
| 5,425,772 A | 6/1995 | Brantigan | |
| 5,433,751 A | 7/1995 | Christel et al. | |
| 5,484,437 A | 1/1996 | Michelson | |
| 5,522,817 A | 6/1996 | Sander et al. | |
| 5,529,075 A | 6/1996 | Clark | |
| 5,562,670 A * | 10/1996 | Brånemark | 606/32 |
| 5,601,565 A | 2/1997 | Huebner | |
| 5,607,424 A | 3/1997 | Tropiano | |
| 5,609,635 A | 3/1997 | Michelson | |
| 5,626,861 A | 5/1997 | Laurencin et al. | |
| 5,645,596 A | 7/1997 | Kim et al. | |
| 5,650,108 A | 7/1997 | Nies et al. | |
| 5,669,909 A | 9/1997 | Zdeblick et al. | |
| 5,702,449 A | 12/1997 | McKay | |
| 5,722,978 A | 3/1998 | Jenkins, Jr. et al. | |
| 5,728,159 A | 3/1998 | Stroever et al. | |
| 5,766,251 A | 6/1998 | Koshino | |
| 5,766,618 A | 6/1998 | Laurencin et al. | |
| 5,776,199 A | 7/1998 | Michelson | |
| 5,865,845 A | 2/1999 | Thalgott | |
| 5,895,426 A | 4/1999 | Scarborough et al. | |
| 5,899,939 A | 5/1999 | Boyce et al. | |
| 5,984,967 A | 11/1999 | Zdeblick et al. | |
| 5,989,289 A | 11/1999 | Coates et al. | |
| 6,008,433 A | 12/1999 | Stone | |
| 6,039,762 A | 3/2000 | McKay | |
| 6,077,989 A | 6/2000 | Kandel et al. | |
| 6,086,593 A | 7/2000 | Bonutti | |
| 6,099,531 A | 8/2000 | Bonutti | |
| 6,102,950 A | 8/2000 | Vaccaro | |
| 6,117,456 A * | 9/2000 | Lee et al. | 424/602 |
| 6,136,032 A | 10/2000 | Viladot Perice et al. | |
| 6,139,585 A | 10/2000 | Li | |
| 6,143,033 A | 11/2000 | Paul et al. | |
| 6,165,203 A | 12/2000 | Krebs | |
| 6,187,047 B1 | 2/2001 | Kwan et al. | |
| 6,203,574 B1 | 3/2001 | Kawamura | |
| 6,227,149 B1 | 5/2001 | Host et al. | |
| 6,241,771 B1 | 6/2001 | Gresser et al. | |
| 6,277,149 B1 | 8/2001 | Boyle et al. | |
| 6,281,257 B1 | 8/2001 | Ma et al. | |
| 6,283,997 B1 | 9/2001 | Garg et al. | |
| 6,296,667 B1 | 10/2001 | Johnson et al. | |
| 6,302,913 B1 * | 10/2001 | Ripamonti et al. | 623/16.11 |
| 6,323,146 B1 | 11/2001 | Pugh et al. | |
| 6,331,312 B1 | 12/2001 | Lee et al. | |
| 6,332,779 B1 | 12/2001 | Boyce et al. | |
| 6,333,029 B1 | 12/2001 | Vyakarnam et al. | |
| 6,340,648 B1 | 1/2002 | Imura et al. | |
| 6,371,988 B1 | 4/2002 | Pafford et al. | |
| 6,376,573 B1 * | 4/2002 | White et al. | 523/115 |
| 6,391,031 B1 | 5/2002 | Toomey | |
| 6,406,498 B1 | 6/2002 | Tormala et al. | |
| 6,432,106 B1 | 8/2002 | Fraser | |
| 6,447,544 B1 | 9/2002 | Michelson | |
| 6,458,162 B1 | 10/2002 | Koblish et al. | |
| 6,503,278 B1 | 1/2003 | Pohjonen et al. | |
| 6,503,279 B1 | 1/2003 | Webb et al. | |
| 6,524,345 B1 | 2/2003 | Valimaa et al. | |
| 6,527,810 B2 | 3/2003 | Johnson et al. | |
| 6,530,955 B2 | 3/2003 | Boyle et al. | |
| D472,972 S | 4/2003 | Anderson | |
| 6,565,572 B2 * | 5/2003 | Chappius | 600/300 |
| 6,575,982 B1 | 6/2003 | Bonutti | |
| 6,595,998 B2 | 7/2003 | Johnson et al. | |
| 6,616,698 B2 | 9/2003 | Scarborough | |
| 6,620,195 B2 * | 9/2003 | Goble et al. | 623/13.14 |
| 6,673,075 B2 | 1/2004 | Santilli | |
| 6,676,703 B2 | 1/2004 | Biscup | |
| 6,686,437 B2 | 2/2004 | Buchman et al. | |
| 6,696,073 B2 | 2/2004 | Boyce et al. | |
| 6,702,821 B2 | 3/2004 | Bonutti | |
| 6,716,245 B2 | 4/2004 | Pasquet et al. | |
| 6,726,722 B2 | 4/2004 | Walkenhorst et al. | |
| 6,731,988 B1 | 5/2004 | Green | |
| 6,733,535 B2 | 5/2004 | Michelson | |
| 6,736,849 B2 | 5/2004 | Li et al. | |
| 6,749,636 B2 | 6/2004 | Michelson | |
| 6,761,739 B2 | 7/2004 | Shepard | |
| 6,770,078 B2 | 8/2004 | Bonutti | |
| D497,993 S | 11/2004 | Dixon et al. | |
| 6,840,961 B2 | 1/2005 | Tofighi et al. | |
| 6,843,807 B1 | 1/2005 | Boyce et al. | |
| 6,863,899 B2 | 3/2005 | Koblish et al. | |
| 6,916,321 B2 | 7/2005 | TenHuisen et al. | |
| 6,921,402 B2 | 7/2005 | Contiliano et al. | |
| 7,238,203 B2 | 7/2007 | Bagga et al. | |
| 7,250,055 B1 * | 7/2007 | Vanderwalle | 606/92 |
| 7,300,439 B2 * | 11/2007 | May | 606/326 |
| 7,713,272 B2 * | 5/2010 | Roller et al. | 606/77 |
| 2002/0037799 A1 | 3/2002 | Li et al. | |
| 2002/0169066 A1 | 11/2002 | Cassidy et al. | |
| 2003/0083662 A1 * | 5/2003 | Middleton | 606/72 |
| 2003/0144743 A1 | 7/2003 | Edwards et al. | |
| 2003/0167093 A1 | 9/2003 | Xu et al. | |
| 2003/0233147 A1 | 12/2003 | Nicholson et al. | |
| 2004/0002770 A1 | 1/2004 | King et al. | |
| 2004/0093089 A1 | 5/2004 | Ralph et al. | |
| 2004/0115172 A1 | 6/2004 | Bianchi et al. | |
| 2004/0225292 A1 * | 11/2004 | Sasso et al. | 606/73 |
| 2004/0243242 A1 | 12/2004 | Sybert et al. | |
| 2005/0070905 A1 | 3/2005 | Donnelly et al. | |
| 2006/0106390 A1 * | 5/2006 | Jensen et al. | 606/73 |
| 2006/0121084 A1 | 6/2006 | Borden et al. | |
| 2006/0199876 A1 | 9/2006 | Troczynski et al. | |
| 2007/0038303 A1 | 2/2007 | Myerson et al. | |
| 2008/0125637 A1 * | 5/2008 | Geist et al. | 600/372 |
| 2009/0138096 A1 | 5/2009 | Myerson et al. | |
| 2010/0042167 A1 * | 2/2010 | Nebosky et al. | 606/315 |
| 2011/0190903 A1 | 8/2011 | Borden et al. | |

OTHER PUBLICATIONS

Ara et al., Effect of blending calcium compounds on hydrolytic degradation of poly (DL-lactic acid-co-glycolic acid), Biomaterials 23 (2002) pp. 2479-2483.

Borden et al., "Structural and human cellular assessment of a novel microsphere-based tissue engineered scaffold for bone repair", Biomaterials 24 (2004) pp. 597-609.

Borden et al., "Tissue engineered microsphere-based matrices for bone repair: design and evaluation", Biomaterials 23 (2002) pp. 551-559.

Borden, et al. "The sintered microsphere matrix for bone tissue engineering: In vitro osteoconductivity studies", ©2002 Wiley Periodicals, Inc. (pp. 421-429).

Böstman, "Clinical biocompatibility of biodegradable orthopaedic implants for internal fixation: a review", Biomaterials 21 (2000) pp. 2616-2621.

Böstman, et al., "Adverse Tissue Reactions to Bioabsorbable Fixation Devices", Clinical Orthopaedics and Related Research 371 (Feb. 2000) pp. 216-227.

Chu et al., "Scanning electron microscopic study of the hydrolytic degradation of poly(glycolic acid) suture", Journal of Biomedical Research, vol. 16, (1982) pp. 417-430.

Chu, "The in-vitro degradation of poly(glycolic acid) sutures—effect of pH", Journal of Biomedical Materials Research, V.15 (1981) pp. 795-804.

Gautier et al., "Poly (α-hydroxyacids) for application in the spinal cord: Resorbability and biocompatibility with adult rat Schwann cells and spinal cord", (1998) pp. 642-654.

Koskikare et al., "Fixation of osteotomies of the distal femur with absorbable, self-reinforced, poly-L-lactide plates—An experimental study on rabbits", Arch Orthop Trauma Surg 116 (1997) pp. 352-356.

Leenslag et al., "Resorbable materials of poly (L-lactide). VI. Plates and screws for internal fracture fixation", Biomaterials vol. 8 (Jan. 1987) pp. 70-73.

Mäkelä et al., "Healing of Physeal Fracture after Fixation with Biodegradable Self-Reinforced Polyglycolic Acid Pins. An Experimental Study on Growing Rabbits", Clinical Materials, (1990) pp. 1-12.

Myerson, "The Use of Osteotomy to Correct Foot and Ankle Deformities", Foot and Ankle Disorders, 2000, vol. 2 Chapter 41, pp. 999-1016.

Rovinsky et al., Case Report, "Osteolytic Reaction to Polylevolactic Acid Fracture Fixation", www.orthobluejournal.com, vol. 24, No. 2 (Feb. 2001) pp. 177-179.

Taylor et al., "Six Bioabsorbable Polymers: In Vitro Acute Toxicity of Accumulated Degradation Products", Journal of Applied Biomaterials, vol. 5, pp. (1994) 151-157.

Tencer et al. "Mechanical and bone ingrowth properties of a polymer-coated, porous, synthetic, coralline hydroxyapatite bone-graft material", Annals of the New York Academy of Sciences 1988 United States, vol. 523, 1988, pp. 157-172, XP009060816 ISSN: 0077-8923 "Introduction" and "Summary".

Tencer et al., "Bone Ingrowth into Polymer Coated Porous Synthetic Coralline Hydroxyapatite", IEEE/Engineering in Medicine and Biology Society Annual Conference 8th. 1986 IEEE, New York, NY, USA, 1986, pp. 1668-1671, XP009060826 abstract.

Tencer et al. "Compressive Properties of Polymer Coated Synthetic Hydroxyapatite for Bone Grafting", Jounral of Biomedical Materials Research, vol. 19, 957-969 (1985).

Törmälä et al., "Ultra-high-strength absorbable self-reinforced polyglycolide (SR-PGA) composite rods for internal fixation of bone fractures: In vitro and in vivo study", Journal of Biomedical Materials Research, vol. 25 (1991) 1-22.

Tuompo et al., "Comparison of polylactide screw and expansion bolt in bioabsorbable fixation with patellar tendon bone graft for anterior cruciate ligament rupture of the knee", Knee Surg, Sports Traumatol, Arthrosc (1999) pp. 296-302.

Vainionpää et al., "Strength and strength retention in vitro, of absorbable, self-reinforced polyglycolide (PGA) rods for fracture fixation", Biomaterials, vol. 8 (Jan. 1987) pp. 46-48.

Vanore et al., "Diagnosis and Treatment of First Metatarsophalengeal Joint Disorders. Section 1: Hallux Valgus", May/Jun. 2003. The Journal of Foot & Ankle Surgery, vol. 42, No. 3, pp. 112-123.

Vanore et al., "Diagnosis and Treatment of First Metetarsophalengeal Joint Disorders. Section 2: Hallux Valgus", May/Jun. 2003. The Journal of Foot & Ankle Surgery, vol. 42, No. 3, pp. 124-136.

* cited by examiner

CONTINUOUS PHASE COMPOSITIONS FOR ACL REPAIR

CROSS-REFERENCE TO RELATED APPLICATIONS

This application is a continuation-in-part of U.S. patent application No. 11/008,075, filed on Dec. 9, 2004, now U.S. Pat. No. 7,879,109, issued on Feb. 1, 2011. The disclosure of the above application is incorporated herein by reference.

INTRODUCTION

The statements in this section merely provide background information related to the present disclosure and may not constitute prior art.

In general, the human musculoskeletal system is composed of a variety of tissues including bone, ligaments, cartilage, muscle, and tendons. Tissue damage or deformity stemming from trauma, pathological degeneration, or congenital conditions often necessitates surgical intervention to restore function. During these procedures, surgeons can use orthopedic implants to restore function to the site and facilitate the natural healing process.

When a ligament becomes detached from a bone, surgery usually is required to reconstruct the ligament. The reconstruction of ligaments, including anterior cruciate ligaments (ACL) and posterior cruciate ligaments (PCL) using autologous ligament grafts, allografts, or artificial grafts, is well known. The ACL and PCL procedures may be performed arthroscopically and, generally, involve preparing a bone tunnel through the tibia and adjacent femur, placing a ligament graft extending between the two bone tunnels, and securing each end of the graft within its respective tunnel. Various methods of graft attachment are known, including the use of interference screws to secure the graft against the wall of the graft tunnel. A metal interference screw may be used to wedge a graft bone block to the wall of the graft tunnel. If a bioabsorbable interference screw is used, the graft may be wedged directly against the bone by the interference screw, without a bone block.

Interference screws are generally composed of non-resorbable metals, ceramics, polymers, and composites. Interference screws for anchoring ligaments to bone are typically fabricated from medically approved metallic materials that are not naturally absorbed by the body. A disadvantage of such interference screws is that once healing is complete, an additional surgical procedure may be required to remove the interference screw from the patient. Metallic interference screws may include a threaded shank joined to an enlarged head having a transverse slot or hexagonal socket formed therein to engage a similarly configured, single blade or hexagonal rotatable driver for turning the interference screw into the bone. The enlarged heads on such interference screws can protrude from the graft tunnel and can cause chronic irritation and inflammation of surrounding body tissue.

Permanent metallic interference screws in movable joints can, in certain instances, cause abrading of ligaments during normal motion of the joint. Interference screws occasionally back out after insertion, protruding into surrounding tissue and causing discomfort. Furthermore, permanent metallic interference screws and fixation devices may shield the bone from beneficial stresses after healing. It has been shown that moderate periodic stress on bone tissue, such as the stress produced by exercise, helps to prevent decalcification of the bone. Under some conditions, the stress shielding which results from the long term use of metal bone fixation devices can lead to osteoporosis.

However, in some instances, it may be desirable to have an interference screw made of resorbable material. These bioabsorbable, resorbable, or biodegradable materials are characterized by the ability to be chemically broken down into harmless by-products that are metabolized or excreted by the body. Materials of this type can offer an advantage over conventional non-resorbable implant materials. A bioabsorbable interference screw provides the required function until the tissue is healed, and once the role of the screw is complete, it is resorbed by the body. The end result is healthy tissue with no signs that an implant was ever present.

Biodegradable or bioabsorbable interference screws have been proposed to avoid the necessity of surgical removal after healing. Because the degradation of a biodegradable screw occurs over a period of time, the support load is transferred gradually to the bone as it heals reducing potential stress shielding effects. Conventional bioabsorbable interference screws are softer and weaker than metallic compositions such that they are not self-tapping, thereby requiring the holes drilled into the bone to be tapped. The necessity to tap holes in the injured bone adds to the complexity of the surgical procedure and lengthens the time required to complete the operation.

Considerable effort has been expended to increase the stiffness and strength of bioabsorbable materials through various composite technologies, such as incorporating strong, stiff, non-absorbable, inorganic structural fibers or particles made from carbon or glass, as reinforcing agents in a bioabsorbable polymeric matrix. The disadvantage of this approach is that the non-absorbable fibers remain in the body tissue after the bioabsorbable polymer has been absorbed and may migrate or cause tissue inflammation. Composite bioabsorbable screws may also be prepared by incorporating inorganic, bioabsorbable glass or ceramic reinforcement fibers or particles in a bioabsorbable polymeric matrix. However, lack of reinforcement-to-matrix interfacial bonding leads to poor load transfer between the reinforcement and the matrix. The weakness of the interface is accentuated when the implants are placed in the human body and may result in compromised long-term performance.

Reinforced bioabsorbable composite screws have also been made by adding an organic bioabsorbable reinforcing fiber to a bioabsorbable polymer matrix. Similarly, highly drawn fibers of PLA or PGA can be fused to form a bioabsorbable polymeric screw with increased stiffness and strength. Unfortunately, the consolidation or the melting temperature of the matrix usually causes the organic biocompatible reinforcing fibers to partially relax their molecular orientation, thereby losing their strength and stiffness and adversely affecting the properties of the composite. Until now, the efforts to utilize bioabsorbable materials for orthopedic load-bearing applications have not been entirely successful.

SUMMARY

Various embodiments of the present technology provide an implantable bioabsorbable interference screw, also referred to herein as an implant, for use in soft tissue repair. The interference screw comprises a bioabsorbable body, which has a plurality of interconnecting pores. The plurality of interconnecting pores in the bioabsorbable body is substantially filled with a bioresorbable polymer. In various embodiments, the interference screw has an instrument interface on one end and a thread starting at a tapered distal end. Methods of use of the implantable bioabsorbable interference screw and kits that include at least one bioabsorbable interference screw are also provided.

It has been found that compositions, devices, and methods of the present technology provide advantages over compositions, devices, and methods among those in the art. Such advantages may include one or more of ease of surgical implementation, increased strength of ligament repair, reduced healing time, and decreased surgical side effects.

Further areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way.

Figure 1:
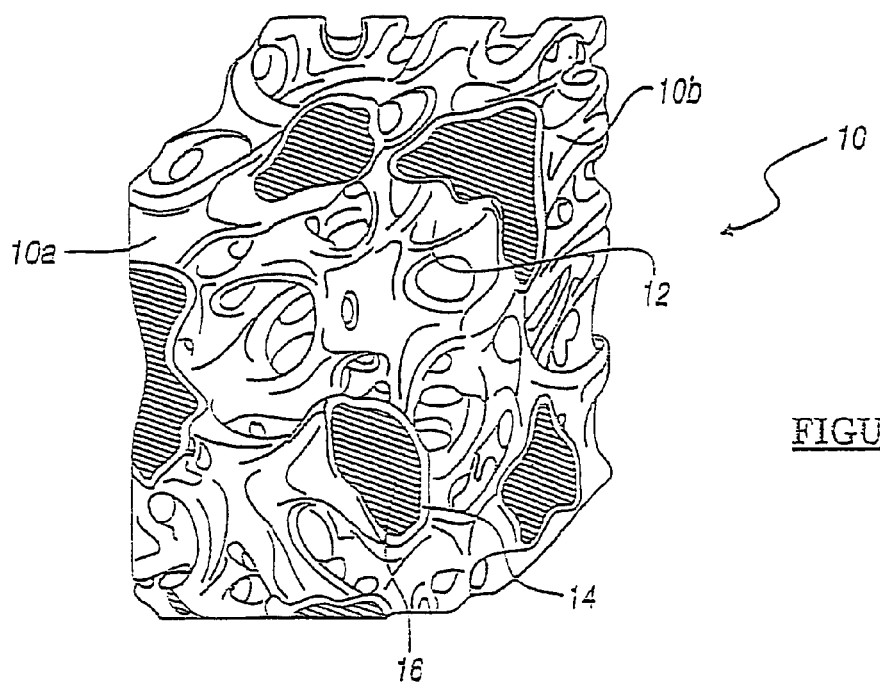
FIG. 1 is a perspective detailed view of a scaffold according to various embodiments.

It should be noted that the drawings set forth herein are intended to exemplify the general characteristics of devices, materials, and methods among those of this technology, for the purpose of the description of such embodiments herein. These drawings may not precisely reflect the characteristics of any given embodiment, and are not necessarily intended to define or limit specific embodiments within the scope of this technology.

DESCRIPTION

The following description of technology is merely exemplary in nature of the subject matter, manufacture and use of one or more inventions, and is not intended to limit the scope, application, or uses of any specific invention claimed in this application or in such other applications as may be filed claiming priority to this application, or patents issuing therefrom. The following definitions and non-limiting guidelines must be considered in reviewing the description of the technology set forth herein.

The headings (such as "Introduction" and "Summary") used herein are intended only for general organization of topics within the disclosure of the teachings, and are not intended to limit the disclosure of the teachings or any aspect thereof. In particular, subject matter disclosed in the "Introduction" may include aspects within the scope of the novel technology and may not constitute a recitation of prior art. Subject matter disclosed in the "Summary" is not an exhaustive or complete disclosure of the entire scope of this technology or any embodiments thereof. Classification or discussion of a material within a section of this specification as having a particular utility (e.g., as being a "bone ingrowth promoting agent" component) is made for convenience, and no inference should be drawn that the material must necessarily or solely function in accordance with its classification herein when it is used in any embodiments of the present technology.

The citation of references herein and during prosecution of this application does not constitute an admission that those references are prior art or have any relevance to the patentability of the technology disclosed herein. Any discussion of the content of references cited is intended merely to provide a general summary of assertions made by the authors of the references, and does not constitute an admission as to the accuracy of the content of such references. All references cited in the "Description" section of this specification are hereby incorporated by reference in their entirety.

The description and specific examples, while indicating embodiments of the technology, are intended for purposes of illustration only and are not intended to limit the scope of the technology. Moreover, recitation of multiple embodiments having stated features is not intended to exclude other embodiments having additional features, or other embodiments incorporating different combinations of the stated features. Specific examples are provided for purposes of illustration only of how to make and use the devices and methods of this technology and, unless explicitly stated otherwise, are not intended to be a representation that given embodiments have, or have not, been made or tested.

As used herein, the word "include" and its variants is intended to be non-limiting, such that recitation of items in a list is not to the exclusion of other like items that may also be useful in the materials, compositions, devices, and methods of these teachings. The terms "a" and "an" mean at least one. Also, all compositional percentages are by weight of the total composition, unless otherwise specified.

The present technology provides medical implants, in particular including implantable screws, comprising a bioabsorbable structure material having a plurality of interconnecting pores and bioresorbable polymer filling at least a portion of said plurality of interconnecting pores. For ease of discussion, FIGS. 4-10 and 13-14 depict representative medical implants. It is understood, however, that the present technology encompasses a wide variety of implants, used for a wide variety of therapeutic and cosmetic applications, in human or other animal subjects. The specific devices and materials used must, accordingly, be biomedically acceptable. As used herein, such a "biomedically acceptable" component is one that is suitable for use with humans or other animals without undue adverse side effects (such as toxicity, irritation, and allergic response) commensurate with a reasonable benefit/risk ratio.

Screw Body Composition

With reference to FIG. 1, a structure 10 for an implantable screw body structure is illustrated. In various embodiments, the structure 10 may be formed of natural sources of biocompatible, bioresorbable and/or bioabsorbable materials, such as coral. In various embodiments, synthetic materials may be used to form the structure 10. These materials may include absorbable ceramics, absorbable polymers, or any other absorbable porous matrix. In various embodiments, the porous material may include the bioresorbable ceramic sold under the trade name Pro Osteon 500R™ by Interpore Spine Ltd. (Irvine, Calif., USA), Pro Osteon 200R™ by Interpore Spine Ltd. (Irvine, Calif., USA), Calcigen PSI™ by Biomet (Warsaw, Ind., USA), or OsteoStim™ by EBI (Parsippanny, N.J., USA). Porous materials useful herein include those disclosed in U.S. Pat. No. 4,976,736, White et al., issued Dec. 11, 1990; and U.S. Pat. No. 6,376,573 White et al, issued Apr. 23, 2002, which are hereby incorporated by reference.

The Pro Osteon material consists of an interconnected or continuous porous calcium carbonate substrate with a thin surface layer of hydroxyapatite. Various other exemplary porous materials may include calcium carbonate, tricalcium phosphate, biphasic calcium phosphate, or any appropriate calcium based ceramic. It will also be understood that the structure 10 may be any appropriate combination of materials, such as including one material as a coating on another.

In various embodiments, the structure 10 may be formed from a polymer. A polymer matrix may define a porous structure similar to the structure 10. The material of the polymer matrix may be any appropriate polymer such as a biocompatible, bioresorbable and/or bioabsorbable polymer, including those discussed herein. Thus, it will be understood that the structure 10 may be formed of any appropriate material, including a resorbable ceramic, a polymer, a composite, and combinations thereof, etc.

The structure 10 itself may be used for various purposes, such as a bone regeneration scaffold or bone graft replacement. Nevertheless, the physical properties of the structure 10 can be augmented for various reasons. For example, the structure 10 alone may not include a selected physical property, such as a selected compressive strength, tensile strength, torsion strength, or the like. Thus, the structure 10 may be augmented to improve its properties allowing for greater use as a surgical device, as discussed herein in various embodiments.

To augment the structure 10, a second material 21 may be added thereto, such as during formation of the structure 10 itself or at a later time. For example, the second material 21 may be injected into or otherwise provided into a plurality of pores 16 defined by the structure 10. The structure 10 can include a channel or plurality of pores 16 that may be substantially continuous or interconnected pores 16. The pores 16 may define a plurality of sizes of pores or porous structures. For example, the pores 16 may range from about 0.1 nanometers (nm) to about 1 mm.

It will be understood that the pores 16 may be any opening that allows access to the interior of the structure 10. For example, there may be interstitial spaces defined between the portions that defined the channels interconnecting other pores 16. In various embodiments, the pores 16 define a generally interconnected path throughout the structure 10. The pores 16 may be connected with other pores 16 or channels to form the interconnected or continuous pores 16 or channels. Also the various channels may be interconnected such that more than a single channel or two openings may be interconnected in the structure 10. The interconnected nature of the pores 16 may be referred to as a continuous phase throughout the structure 10. The continuous phase may also be understood to be interconnected pores 16 that are defined by a solid portion of the structure 10. Moreover, in various embodiments, the pores 16 generally extend through the structure 10 such that a path can be traced from a first side 10a of the structure 10 to a second side 10b of the structure, or from an entrance path to an exit path that can enter and exit from any sides, or from the same side.

Figure 2:
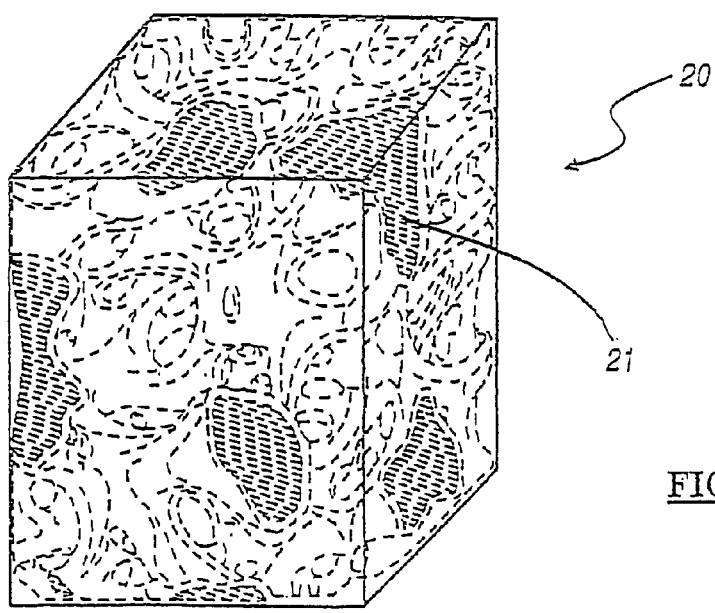
FIG. 2 is a perspective detailed view of a continuous phase composite according to various embodiments.

The different sized pores 16 or channels may be used with or are specifically applicable to different types of surgical indications. For example, with reference to FIG. 2, the pores 16, such as those generally ranging from about 10 nm to about 1 mm, may be filled with the second material 21, which may be, for example, a selected polymer. Macroporosity, as used herein, relates to the structure 10 comprising pores 16 with diameters about 100 µm or greater. Mesoporosity, as used herein, relates to structure 10 comprising pores 16 with diameters that range from about 10 µm to about 100 µm. Microporosity, as used herein, relates to the structure 10 comprising pores 16 with diameters from about 10 µm to less than 0.01 µm. In various embodiments, structure 10 may comprise pores 16 that have macroporosity, mesoporosity, microporosity, or combinations thereof. In various embodiments, structure 10 may comprise pores 16 having a diameter of about 190 microns to about 230 microns, and an exemplary structure 10 useful herein may be Pro Osteon 200R™ by Interpore Spine Ltd. (Irvine, Calif., USA). In various embodiments, structure 10 may comprise pores 16 with diameters of about 350 microns to about 600 microns and an exemplary structure 10 may be Pro Osteon 500R™ by Interpore Spine Ltd. (Irvine, Calif., USA). In various embodiments, the surface of pores 16 may comprise a coating 14, and examples of coating 14 useful herein may include calcium sulfate, calcium carbonate, and/or calcium phosphate. The second material 21 may be injection molded in a semi-liquid, molten form to fill the macroporosity defined by the structure 10, such as the pore 16 sizes that are operable or easily filled with the polymer in a flowable state. Various polymers may be used as the second material 21 to fill a selected porosity of the structure 10. For example, bioabsorbable, bioabsorbable, biocompatible materials, or any appropriate combination of materials may be used.

Suitable absorbable materials useful for structure 10 may include, but are not limited to, glasses or ceramics comprising mono-, di-, tri-, α-tri-, β-tri-, and tetra-calcium phosphate, hydroxyapatite, calcium sulfates, calcium oxides, calcium carbonates, magnesium calcium phosphates, phosphate glass, bioglass, mixtures thereof or a stiff, strong polymer, such as a PLA polymer.

In various embodiments, the second material 21 may include PLA. For example, PLA may be provided that includes a compositional ratio of about 70:30 poly(L/D,L lactic acid). The specific ratio of various chiral monomers in the polymer is merely exemplary and any appropriate ratio may be used. Nevertheless, herein the 70:30 poly(L/D,L lactic acid) may be referred to as PLDLLA. Other polymers may include a copolymer of lactic acid and glycolic acid. It will be understood, however, that any appropriate polymer material may be used as the second material 21 to form the composite 20. Other bioresorbable, biocompatible polymers include poly(glycolic acid), poly(carbonate), poly(urethane), poly (amino acids), poly(phosphazenes), poly(hydroxyacids), poly(anhydrides), poly(dioxanone), poly(hydroxybutyrate), and poly(caprolactone). Also, copolymers of these or other appropriate monomers may be used. Further, as discussed above, the structure 10 may be formed of a polymer matrix including these polymers or copolymers. The selected polymer that may be used with the structure 10, however, may be injection molded or otherwise fill the pores 16 defined by the structure 10. The second material 21 may fill the pores 16 of the structure 10 to form a substantially solid structure. Nevertheless, the composite 20 may still include a selected porosity or open pores 16 or channels even when filled with the second material 21. Also, it may be selected to fill the pores 16 less than completely, therefore, leaving an open space in at least a portion of the pores 16 even if they may include some of the second material 21. For example, pores 16 having a size of about 0.01 µm to about 10 µm may still remain in the composite 20 after the second material 21 is injected for the second material 21 fills the larger pores 16 or macro pores of the structure 10. The pores 16 that are generally less than about 10 µm, may be referred to herein as micropores or microporosity. The microporosity, however, is not necessary and may not always be present. For example, with various polymer filling techniques, such as polymerization of a positioned monomer discussed herein, the microporosity may be substantially less or non-existent in the composite 20. As is generally understood, a polymer is generally formed of a single monomer while a copolymer generally includes at least two types of monomers.

In various embodiments, suitable materials useful for the second material. 21 include biocompatible polymers selected from the group consisting of aliphatic polyesters, polyorthoesters, polyanhydrides, polycarbonates, polyurethanes, polyamides, polyalkylene oxides, and combinations thereof. In various embodiments, the second material 21 may be formed from aliphatic polymers, polyesters, copolymer polyesters and blends thereof. The aliphatic polyesters are typically synthesized in a ring opening polymerization. Suitable monomers include, but are not limited to, lactic acid, lactide (including L-, D-, meso and D,L mixtures), glycolic acid, glycolide, ϵ-carprolactone, p-dioxanone (1,4-dioxan-2-one), trimethylene carbonate (1,3-dioxan-2-one), δ-valerolactone, β-butyrolactone, ϵ-decalactone, 2,5-diketomorpholine, pivalolactone, α,α-diethylpropiolactone, ethylene carbonate, ethylene oxalate, 3-methyl-1,4-dioxane-2,5-dione, 3,3-diethyl-1,4-dioxan-2,5-dione, gamma-butyrolactone, 1,4-dioxepan-2-one, 1,5-dioxepan-2-one, 6,6-dimethyl-dioxepan-2-one, 6,8-dioxabicycloctane-7-one, and combinations thereof. These monomers generally are polymerized in the presence of an organometallic catalyst and an initiator at elevated temperatures.

In various embodiments, the composition of the implantable screw is selected to optimize one or more selected properties, such as a compressive strength after a selected time period after implantation, or the amount of time generally necessary for bone ingrowth to form a selected fusion. Therefore, a polymer may be chosen for the second material 21 of the composite 20. For example, the PLDLLA second material 21, discussed above, may form about 60% of the composite 20 with about 40% of the composite 20 being the structure 10 formed of the Pro Osteon 500R ™. Such a combination can achieve a compressive strength of about 1500 N to about 3000 N at about 6 months after implantation. In various embodiments, other second materials 21 and other structures 10 may be used to achieve similar results or varying results to meet the needs of the composite 20.

In various embodiments, a fast resorption of the composite 20 may be selected. For example, in a fracture, healing or repair may be faster than in a fusion. Therefore, an interference screw that is substantially resorbed after about 3 months to about 6 months may be selected. Such an implant may be formed with a copolymer of lactic acid and glycolic acid. The copolymer can be about 85% lactic acid and about 15% glycolic acid, similar to the material sold as Lacotsorb™ by Biomet, Inc. An implantable screw or implant, including such a copolymer, can be about 60% of the composite 20 while the other about 40% is formed of the Pro Osteon may be used in a fracture situation. For example, an implantable screw or implant (70, 90, 110, 130, 170, 200, 220) may be formed of such a composition for use as an interference screw in an ACL replacement procedure to provide a selected time when the graft is no longer held with the implant (70, 90, 110, 130, 170, 200, 220).

Also, the second material 21 may be a polymer, or a slower resorbing material and, as such, may be selected based upon inherent properties or ones formed therein. For example, a slower resorbing second material 21 may generally be a polymer having a higher molecular weight. Thus, the slower the implant should resorb or the longer a selected property, such as compressive strength is needed, the higher the molecular weight of the polymer that may be chosen for the second material 21. However, it will also be understood that selected second materials 21 may include properties that may be achieved by a polymer having a lower molecular weight. Also, selected strengths of the second material 21 may be inherent in a polymer itself, rather than a selected molecular weight thereof.

In various embodiments, the composite 20 can include a dual ceramic. The structure 10 can be formed of a first ceramic including a first property and the pores 16 or channels may be filled with a second ceramic (second material 21), rather than a polymer, and the second ceramic having a second property. The different properties can include resorption rates, compressive strengths, torsion strengths, or the like. This can be achieved by casting a ceramic slurry into the porosity of the structure 10. The slurry can undergo a chemical reaction to set into a hardened form or it can be sintered to form a rigid ceramic phase.

Also, two polymers that independently may have different properties can be used to form the composite 20. For example, a first polymer, having a first property, may be used to form the structure 10 that includes a selected porosity and/or channels. The porosity of the structure 10 can be filled with the second material 21 (a second polymer) having a second property. Again, the properties of the two polymers may include a compressive strength, a resorption rate, a tensile strength, or the like. This can be achieved through injection molding, in situ polymerization, and solution-casting techniques, as described herein.

It will be understood that the composite 20 may be a substantially dual phase or greater composite 20 so that it will react in a substantially uniform manner when implanted in the body. The phases can refer to the phase of the structure 10 and the phase of the second material 21 positioned in the pores 16 or channels of the structure 10, such as a bioresorbable polymer. According to various embodiments, the composite 20 may be about 30 weight percent (wt %) to about 70 wt % the second material 21 (a polymer fill) and about 30 wt % to about 70 wt % structure 10. For example, the composite 20 may be about 55 wt % to about 65 wt % the second material 21 (a polymer fill) and about 45 wt % to about 55 wt % ceramic structure 10. Nevertheless, the composite 20 may be substantially 100 wt % polymer if the structure 10 is formed from a porous polymer matrix. In this case, the composite 20 may be about 30 wt % to about 70 wt % the second material 21 (a polymer fill) and about 30 wt % to about 70 wt % structure 10, a porous polymer matrix. The same applies to a substantially 100% ceramic composite 20 having both a slow and fast resorbing ceramic.

Both phases, that being the structure 10 phase and the second material 21 phase, may be substantially continuous. This means, according to various embodiments, that the second material 21 phase is substantially interconnected throughout the composite 20 and that structure 10 phase is also substantially interconnected. Such results can be obtained by using an intact structure 10 phase rather than a particle. It will be understood that an appropriate structure 10 phase may be formed from particles. By filling the porosity of the structure 10 phase with the second material 21, the resulting composite 20 is effectively composed of two or more distinct, intact, and continuous phases. As discussed herein, the different resorption rates of the continuous phases (for example, structure 10 and the second material 21) within the composite 20 results in a resorption profile that can include a slowly degrading phase and a quickly degrading phase. The quickly degrading phase can allow for tissue ingrowth as the phase is resorbed whereas the slowly degrading phase provides the implant site with mechanical support. It will be understood that either the structure 10 or the second material 21 may be formed to be the quicker resorbing phase.

The composite 20 is the result of filling the pores 16 of structure 10. However, the pores 16 of the structure 10 can be left open. The microporosity found in the structure 10 of composite 20 may, without being bound by the theory, function in that it allows for the absorption of fluid throughout the composite 20 and the diffusion of degradation products out of the composite 20. This allows the composite 20 to degrade in an even manner from the inside out, results in a gradual transition of load to the newly regenerating tissue. In instances where acid based polymers such as PLA and PGA are used as the second material 21 within the composite 20, the microporosity in the ceramic allows the acidic products to leave the implant and be absorbed by the surrounding tissue in a timely manner.

Figure 3:
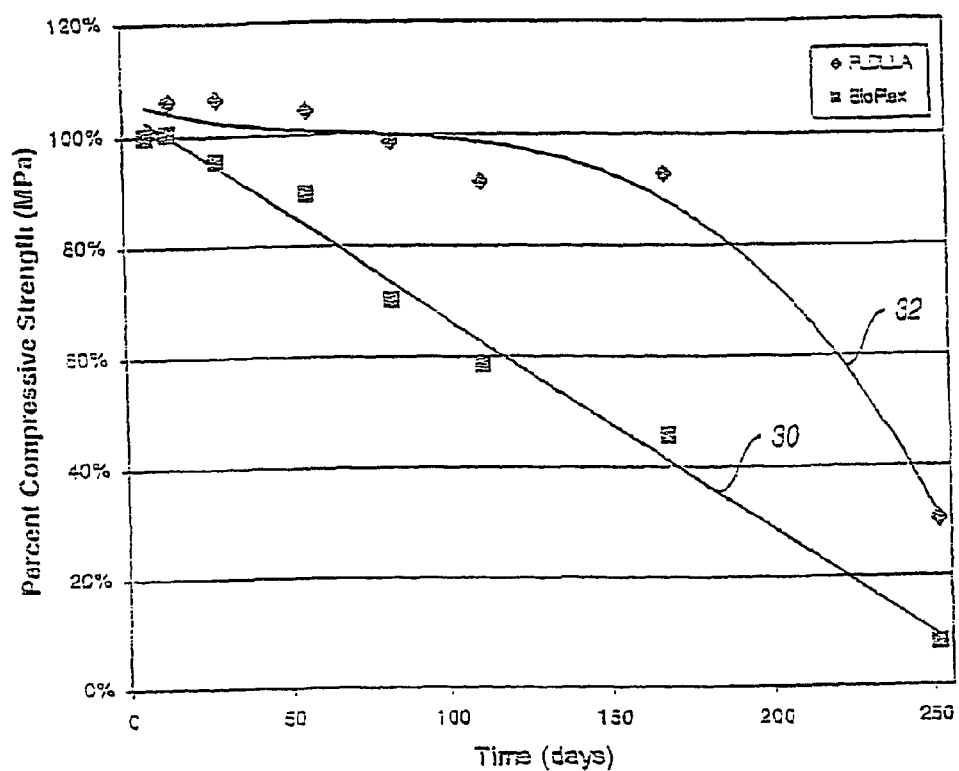
FIG. 3 is a graph comparing compressive strength over time of a continuous phase composite and a pure polymer sample according to various embodiments.

As discussed above, the second material 21 injected into the structure 10 may fill the pores 16 of the structure 10 and yet maintain an open microporosity. The effect of this microporosity and/or continuous phase aspects of the composite 20 on the degradation of a continuous phase composite 20 is shown in FIG. 3. The graph in FIG. 3 illustrates the results of an experiment where degradation was conducted in a generally known phosphate buffer solution held at about body temperature (about 37° C.) The degradation profile of a continuous phase composite 20 composed of PLDLLA (the second material 21) and Pro Osteon 500R™ (structure 10) was compared to a pure polymer sample composed of only PLDLLA. In FIG. 3, the graph of compressive strength over time shows a generally even and linear degradation profile of the composite 20 (line 30) when compared to a faster drop in strength seen with the pure polymer device (line 32). Although the same polymer was used in both the composite 20 and pure polymer specimens, the graph clearly shows the impact of the composite 20.

As illustrated in FIG. 3, in various embodiments, the compressive strength of the pure PLDLLA sample does not change over a significant life span of the implant. Nevertheless, after about 150 days, a drop in compressive strength is illustrated. Therefore, during a majority of the life span of the PLDLLA implant, the compressive strength does not change, however, near the end of the life span of the PLDLLA implant, the compressive strength may degrade rapidly. A more even and linear drop in compressive strength may be selected for various applications. This may allow for an even and gradual loading of an area of the anatomy near the implant of the composite 20.

Examining the composite 20 degradation profile, as illustrated by line 32, the compressive strength of the composite 20 is substantially linear over its lifetime. The degradation of the compressive strength of the composite 20 does not include any long periods of maintenance of a single strength, or a steep drop off at any particular time. A substantially linear decrease in compressive strength over time in the degradative environment, such as an anatomical environment, allows for the gradual loading of healing tissue with additional stresses.

For example, when an implant is used as a bone replacement, it may be desirable to have a substantially continuous increase in stresses relative to the implant. As is known to one skilled in the art, the increase of stresses relative to the bone may increase or enhance bone ingrowth into the area. Particularly, in a resorbable implant, it is desirable to increase or enhance bone ingrowth into the area where the implant has been degraded. As the implant degrades, the stresses are transferred to the surrounding bone, and the new tissue slowly becomes load-bearing.

In various embodiments, the composite 20 exhibits a linear decrease in compressive strength as shown FIG. 3. In addition to the benefits of a gradual transfer of forces to the new tissue, the composite 20 also can be an excellent media for tissue ingrowth into the implant. This ability was demonstrated in a load-bearing bone defect model in the tibia and femur of sheep. In such a model, typical solid polymer implants may show bone formation in limited amounts on the surface of the material. With the continuous phase composite 20, the resorption of the ceramic structure 10 phase may allow eventual growth of bone into the center of the implant wall.

In various embodiments, the interaction of calcium carbonate and lactic acid from the polymer (the second material 21) phase results in a self-neutralizing reaction that eliminates some of the acid released from a degrading implant. This phenomenon further improves the long term biocompatibility of the implant as seen by new bone formation in areas of active lactic acid degradation.

In various embodiments, in addition to the self-neutralizing ability of the composite 20, the presence of vascularized bone and residual microporosity also add to the overall biocompatibility of the degrading of the composite 20. Thus, tissue ingrowth in the pores 16 serves as a means to transport degradation products from the site to the bloodstream. The blood vessels within an implant and the pores 16 system allow degradation products to be cleared from the implant area in a timely manner.

In various embodiments, therapeutic agents are used in conjunction with the composite 20. In general, therapeutic agents which may be administered via the pharmaceutical compositions of the various embodiments include, without limitation: anti-infectives such as antibiotics and antiviral agents; chemotherapeutic agents (i.e. anticancer agents); anti-rejection agents; analgesics and analgesic combinations; anti-inflammatory agents; hormones such as steroids; growth factors, including bone morphogenic proteins (i.e. BMP's 1-7), bone morphogenic-like proteins (i.e. GFD-5, GFD-7 and GFD-8), epidermal growth factor (EGF), fibroblast growth factor (i.e. FGF 1-9), platelet derived growth factor (PDGF), insulin like growth factor (IGF-I and IGF-II), transforming growth factors (i.e. TGF-β I-III), vascular endothelial growth factor (VEGF); and other naturally derived or genetically engineered proteins, polysaccharides, glycoproteins, or lipoproteins.

In various embodiments, the composite 20 may comprise at least one of platelet rich plasma (PRP), concentrated bone marrow aspirate and lipoaspirate cells. In various embodiments, the composite 20 may include hematopoietic stem cells, stromal stem cells, mesenchymal stem cells, endothelial progenitor cells, red blood cells, white blood cells, fibroblasts, reticulacytes, adipose cells, or endothelial cells. Any of the above cells, PRP, and/or concentrated bone marrow aspirate may be obtained by using centrifugation methods and an example of such methods is disclosed in U.S. Patent Application Publication No. 2005/0109716. In various embodiments, composite may be soaked in at least one fraction created by centrifugation. The at least one fraction may include at least one of PRP, concentrated bone marrow aspirate, lipoaspirate cells, hematopoietic stem cells, stromal stem cells, mesenchymal stem cells, endothelial progenitor cells, red blood cells, white blood cells, fibroblasts, reticulacytes, adipose cells, endothelial cells, any other autologous tissue, and combinations thereof.

According to various embodiments, the composite 20 comprises concentrated bone marrow aspirate made by a method for concentrating bone marrow aspirate and blood including collecting bone marrow aspirate and blood from a patient then loading the bone marrow aspirate and blood into a separator that can separate the aspirate and the blood into three or more fractions. The method includes centrifuging the separator containing the bone marrow aspirate and the blood creating a fraction that has a concentrated bone marrow aspirate and/or a concentrated blood. In various embodiments, such a concentration may be referred to as a buffy coat. The method also includes withdrawing the fraction comprising the concentrate or buffy coat.

According to various embodiments, the composite 20 comprises concentrated bone marrow aspirate, blood, and/or a blood fraction. Such materials may be derived by loading bone marrow aspirate and/or blood into a separator that can separate the bone marrow aspirate and/or blood into three or more fractions. The method also includes centrifuging the separator then withdrawing a fraction comprising at least one of the group consisting of buffy coat, hematopoietic stem cells, stromal stem cells, mesenchymal stem cells, endothelial progenitor cells, red blood cells, white blood cells, fibroblasts, reticulacytes, adipose cells, and endothelial cells, and then applying the fraction to an implant according to this technology, and implanting the implant.

Methods of Composite Manufacture

The composite 20 may also be formed by using any appropriate method, including such methods as are known to those skilled in the art. Generally, the second material 21 used to fill the selected porosity is added to the structure 10 or otherwise used to fill the porosity of the structure 10. In various embodiments, injection molding is used to force molten polymer (the second material 21) into the macroporosity of a porous ceramic structure 10. This can result in the composite 20 including approximately 5-10% open microporosity. In various embodiments, vacuum impregnation techniques may be used. Rather than producing a positive pressure on the melted polymer, a relatively low pressure is formed in the structure 10 to pull the second material 21, which may be, for example, a bioresorbable polymer or a combination thereof, into the porosity. Further techniques include solution embedding where the second material 21 is dissolved and then cast into the porosity.

In various embodiments, in situ polymerization techniques where the polymer being used as second material 21 may be polymerized within the porosity of the structure 10 can be used to form the composite 20. When employing in situ polymerization techniques, the structure 10 is submerged in a reaction mixture of a monomer or a plurality of monomers, an initiator, and/or a catalyst and then heated to the reaction temperature. The second material 21 (a polymer) is then formed in situ within the porosity of the structure 10.

Other methods of forming the composite 20 are related to the use of a porous polymer matrix as the structure 10. The ceramic material is cast within a porous, polymer matrix structure that forms the structure 10. A polymer matrix may be formed to include a selected porosity and a ceramic slurry may be positioned in the pores of the matrix. The ceramic slurry may then be forced to harden to form a solid or porous ceramic phase within the porosity of the structure 10. Thus, the composite 20 may be formed by positioning the polymer in the structure 10 formed of a porous ceramic or by positioning a ceramic in the structure 10 formed of a porous polymer.

Screw Implants

Figures 4, 5:
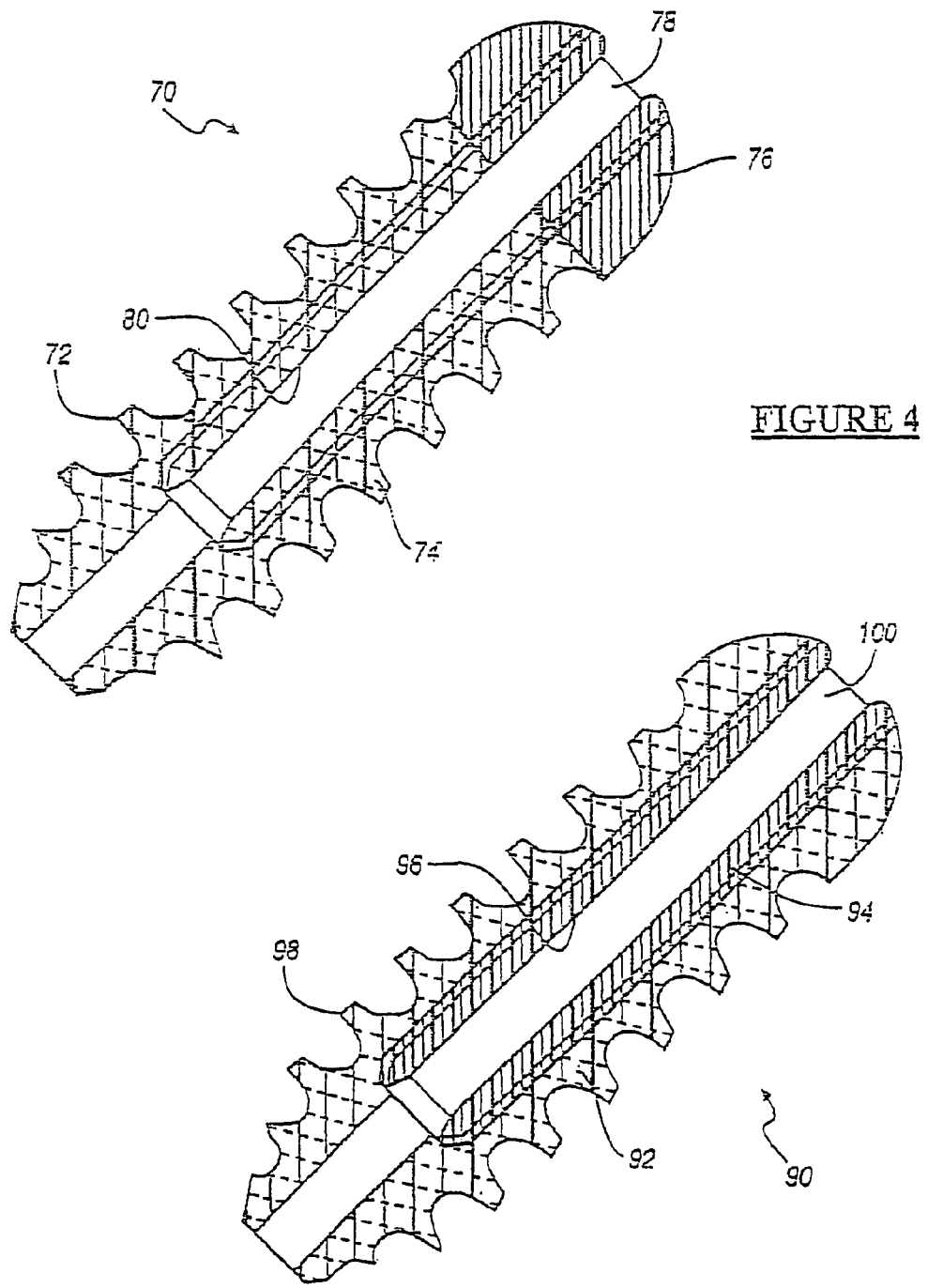
FIG. 4 is an implant according to various embodiments.
FIG. 5 is an implant according to various embodiments.

With reference to FIG. 4, an implant screw embodiment 70 is illustrated. In various embodiments, implant 70 may be an interference screw that can be used to attach soft tissue to bone such as for ligament repair or replacement, as described herein. The implant 70 demonstrates the versatility of the fabrication process by machining devices with both a composite portion 74 which may be composite 20 and a polymer portion 76 which may be the second material 21 or another bioresorbable polymer. For example, the implant 70 may include an external thread or engagement portion 72 composed of the composite portion 74 similar to the composite 20. However, implant 70 can be machined from a composite 20 block with an excess polymer portion 76. This results in a dual region implant 70 with a polymer portion 76 and a composite portion 74. Therefore, the composite portion 74 may be formed from a ceramic material (structure 10), such as the Pro Osteon 500R™, that has been reinforced or injected with a polymer (the second material 21), such as the PLDLLA. Also, the polymer portion 76 may be molded to the composite portion 74 according to various embodiments.

In addition, the polymer portion 76 may be composed of 100% PLDLLA. Such a polymer portion 76 can improve the mechanical properties of the implant 70 for various applications. For example, the polymer portion 76 may provide a torsional strength that is greater than the torsional strength of the composite portion 74. Therefore, a tool engaging portion 78 or area may be formed in the polymer portion 76 to allow for a greater torsional force to be applied to the implant 70 by a driver that may not be satisfied by the composite portion 74. The tool engagement portion 78 may include a hexagonal (hex or Allen), a slot, a square, a tapered square (Robertson), an oval, a cruciform shape, a star (Torx®), a cross (Philips), or the like, that is an open shape through at least a portion of the center of the implant 70. A driver (not shown) is designed to engage with one of the above mentioned open shapes to transfer torque needed to screw implant 70 into a bone tunnel.

With regard to the fabrication of implant 70, this orientation of polymer portion 76 and composite portion 74 can be fabricated by drilling holes within the porous structure 10 and then subjecting the structure 10 to one of the composite fabrication techniques to introduce the second material 21 into the pores 16 of structure 10, as discussed above. The addition of the second material 21 phase to the structure 10 with pores 16, such as through injection molding, results in the filling of the pores 16 in addition to creating the composite 20. During machining, the implant 70 can be centered around a defined bore 80 through the implant 70. The resulting implant 70 will have a polymer portion 76 on top of composite portion 74.

With reference to FIG. 5, an implant screw embodiment 90 is illustrated. In various embodiments, implant 90 may be an interference screw that can be used to attach soft tissue to bone, such as for ligament repair or replacement, as described herein. The implant 90 can also include two regions, such as a composite region 92, which may be composite 20, and a polymer portion 94, which may be the second material 21 or another bioresorbable polymer. The composite region 92 may be substantially similar to the composite 20 illustrated in FIG. 2. The addition of the polymer portion 94 to the central area of the composite portion 92, however, can be used to achieve selected properties of the implant 90. For example, the polymer region 94 may provide a torsional strength that is greater than the torsional strength of the composite portion 92. Therefore, a tool engaging portion 100 or area may be formed in the polymer portion 94 to allow for a greater torsional force to be applied to the implant 90 by a driver (not shown) that may not be satisfied by the composite portion 92. The tool engagement portion 100 may include a hexagonal (hex or Allen), a slot, a square, a tapered square (Robertson), an oval, a cruciform shape, a star (Torx®), a cross (Philips), or the like, that is an open shape through at least a portion of the center of the implant 90. A driver (not shown) is designed to engage with one of the above mentioned open shapes to transfer torque needed to screw implant 90 into a bone tunnel.

With regard to the fabrication of implant 90, this orientation of polymer portion 94 and composite portion 92 can be fabricated by drilling holes within the porous structure 10 and then subjecting the structure 10 to one of the composite fabrication techniques to introduce the second material 21 into the pores 16 of structure 10, as discussed above. The addition of the second material 21 phase to the structure 10 with pores 16, such as through injection molding, results in the filling of the pores 16 in addition to creating the composite 20. During machining, the implant 90 can be centered around the central polymer portion 94 to define a bore 96 through the implant 90. The resulting implant 90 will have a central polymer portion 94 surrounded by a composite portion 92.

The implant 90 may be used for any appropriate purpose, and an engagement portion 98 may be formed on an exterior thereof. The engagement portion 98 may be used to engage various structures, such as bone, such that the implant 90 may be an anchor or may define a screw. Further, a tool engagement portion 100 may be defined in the central polymer portion 94 for allowing engagement of a tool or driver (not shown) with the implant 90 for positioning the implant 90 in various anatomical locations. The implant 90 may be used as a bone anchor, a suture anchor, a soft tissue anchor, a fracture screw, an interference screw, or any appropriate purpose.

Figure 6:
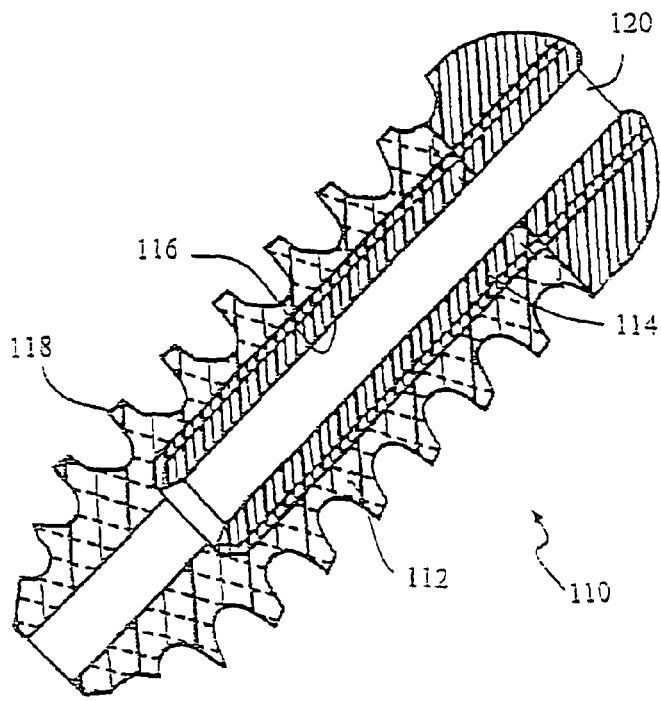
FIG. 6 is an implant according to various embodiments.

With reference to FIG. 6, an implant screw embodiment 110 is illustrated. In various embodiments, implant 110 may be an interference screw that can be used to attach soft tissue to bone such as for ligament repair or replacement, as described herein. The implant 110 demonstrates the versatility of the fabrication process by machining devices with both a composite portion 112 which may be composite 20 and a polymer portion 114 which may be the second material 21 or another bioresorbable polymer. For example, the implant 110 may include an external thread or engagement portion 118 composed of a continuous phase composite that may be similar to the composite 20. However, implant 110 can be machined from a composite 20 block with an excess polymer portion 114. This results in a dual region implant with a polymer portion 114 and a composite portion 112. Therefore, the composite portion 112 may be formed from a ceramic material (structure 10), such as the Pro Osteon 500R™, that has been reinforced or injected with a polymer (the second material 21), such as the PLDLLA. Also, the polymer portion 114 may be molded to the composite portion 112, according to various embodiments.

In addition, the polymer portion 114 may be composed of 100% PLDLLA. Such a polymer portion 114 can improve the mechanical properties of the implant 110 for various applications. For example, the polymer portion 114 may provide a torsional strength that is greater than the torsional strength of the composite portion 112. Therefore, a tool engagement portion 116 or area may be formed in the polymer portion 114 to allow for a greater torsional force to be applied to the implant 110 by a driver that may not be satisfied by the composite portion 112. The tool engagement portion 116 may include a hexagonal (hex or Allen), a slot, a square, a tapered square (Robertson), an oval, a cruciform shape, a star (Torx®), a cross (Philips), or the like, that is an open shape through at least a portion of the center of the implant 110. A driver (not shown) is designed to engage with one of the above mentioned open shapes to transfer torque needed to screw implant 110 into a bone tunnel.

With regard to the fabrication of implant 110, this orientation of polymer portion 114 and composite portion 112 can be fabricated by drilling holes within the porous structure 10 and then subjecting the structure 10 to one of the composite fabrication techniques to introduce the second material 21 into the pores 16 of structure 10, as discussed above. The addition of the second material 21 phase to the structure 10 with pores 16, such as through injection molding, results in the filling of the pores 16 in addition to creating the composite 20. During machining, the implant 110 can be centered around the central tool engagement portion 116 to define a bore 80 through the implant 110. The resulting implant 110 will have a central polymer portion 114 surrounded by a composite portion 112.

Figure 7:
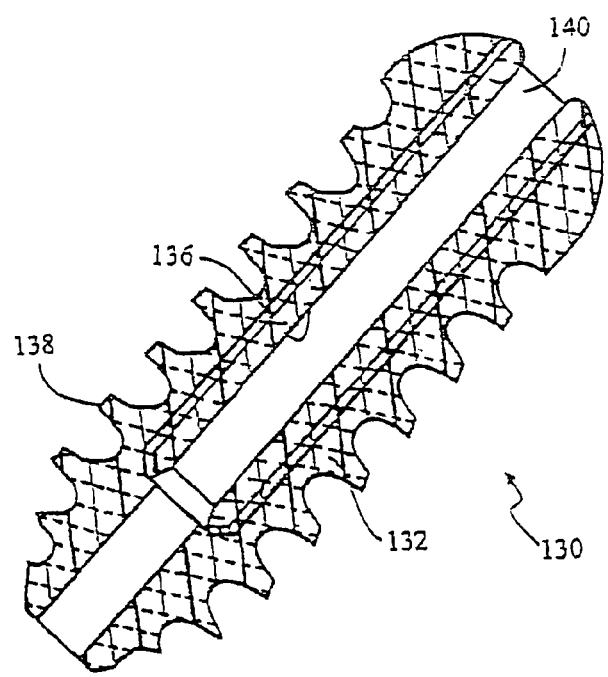
FIG. 7 is an implant according to various embodiments.

With reference to FIG. 7, an implant screw embodiment 130 is illustrated. In various embodiments, implant 130 may be an interference screw that can be used to attach soft tissue to bone, such as for ligament repair or replacement as described herein. The implant 130 can be made as a composite portion 132, which may be composite 20. The composite portion 132 may be substantially similar to the composite 20 illustrated in FIG. 2. Therefore, a tool engaging portion 140 or area may be formed in the composite portion 132 to allow for a torsional force to be applied to the implant 130 by a driver. The tool engagement portion 140 may include a hexagonal (hex or Allen), a slot, a square, a tapered square (Robertson), an oval, a cruciform shape, a star (Torx®), a cross (Philips), or the like, that is an open shape through at least a portion of the center of the implant 130. A driver (not shown) is designed to engage with one of the above mentioned open shapes to transfer torque needed to screw implant 130 into a bone tunnel.

Implant 130 can be fabricated by drilling holes within the porous structure 10 and then subjecting the structure 10 to one of the composite fabrication techniques to introduce the second material 21 into the pores 16 of structure 10, as discussed above. The addition of the second material 21 phase to the structure 10 with pores 16, such as through injection molding, results in the filling of the pores 16 in addition to creating the composite 20. During machining, the implant 130 can be centered around the central tool engagement portion 140 to define a bore 136 through the implant 130. The resulting implant 130 will have a tool engagement portion 140 surrounded by a composite portion 132.

The implant 130 may be used for any appropriate purpose, and an engagement portion 138 may be formed on an exterior thereof. The engagement portion 138 may be used to engage various structures, such as bone, such that the implant 130 may be an anchor or may define a screw. Further, a tool engagement portion 140 may be defined in the composite portion 132 for allowing engagement of a tool with the implant 130 for positioning the implant 130 in various anatomical locations. The implant 130 may be used as a bone anchor, a suture anchor, a soft tissue anchor, a fracture screw, an interference screw, or any appropriate purpose.

In various embodiments, interference screws, such as implant 70, 90, 110, 130 may be sized so that they are slightly larger that the diameter of the tunnel, so that they dilate the bone tunnel upon insertion. Dilation advantageously compacts the soft cancellous bone between the ends of the tunnel, providing better fixation. Conventional straight-sided bioabsorbable interference screws have an interference fit of about 1 mm such that about 1 mm of bone is dilated as the screw is inserted into the bone tunnel.

Implants, such as the implants 70, 90, 110, 130, according to various embodiments, may be formed in many different ways and include different structures. Those described above are merely exemplary in nature and not intended to limit the present teachings herein. For example, an implant 70, 90, 110, 130 may include an exterior thin coat formed around a polymer interior, or vice-versa. The exterior thin coat may include a thickness that is substantially less than that of the interior portion, but provide selected properties to an implant.

Figure 8:
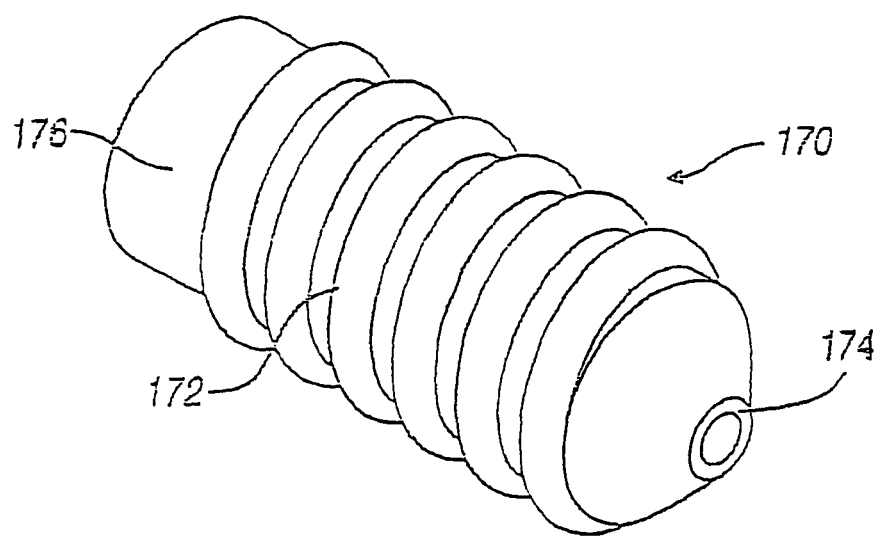
FIG. 8 is an implant according to various embodiments.

With reference to FIG. 8, an implant screw embodiment 170 is illustrated. The implant 170 may define a screw or anchor portion that may be positioned relative to a selected portion of the anatomy. The implant 170 may define a thread 172 that extends along a length of the implant 170 from a first or insertion end 174 to a second or driving end 176. The thread 172 may or may not extend the entire length of the implant 170.

Regardless, the implant 170 may define the thread 172 and the driving end 176 such that the implant 170 may be inserted into a selected portion of the anatomy. Similar to the implants 70, 90, 110, 130 illustrated in FIGS. 4-7 above, the implant 170 may be used to fix a selected soft tissue therein, fix a structure thereto, or other appropriate procedures. For example, in a generally known anterior cruciate ligament replacement, the implant 170 may define an interference screw to assist in holding the graft in a selected position.

The implant 170 may be formed substantially completely of the composite 20. It will be understood that the implant 170 or the implants described above, according to various embodiments, may be provided for various procedures or purposes. As is generally understood in the art, a graft may be positioned or provided of soft tissue to interconnect a femur and a tibia. The implant 170 may be used to substantially hold the soft tissue portion relative to a selected portion of the anatomy. As discussed above, the composite material forming the implant 170 may be absorbed into the anatomy at a selected rate to allow for bone ingrowth and fixation, such as generally anatomical fixation, of the soft tissue may be provided. In various embodiments, implant 170 may comprise a composite region and a polymer region, as well as tool engagement, as illustrated and described above in FIGS. 4-7.

Figure 9:
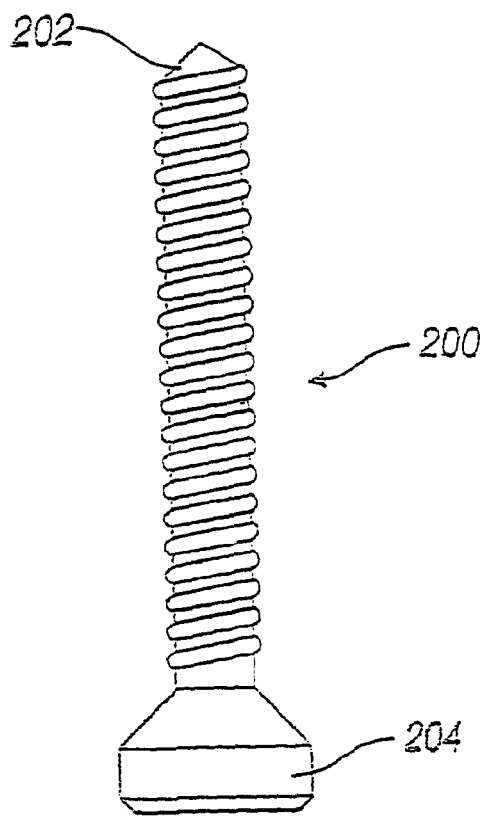
FIG. 9 is an implant according to various embodiments.

An implant screw embodiment 200 in FIG. 9 can be used for fracture repair. In various embodiments, implant 200 may be used as an interference screw in ligament repair or replacement, as described herein. The implant 200 may include an extended shaft that defines a thread 202 along all or a portion of the shaft. A driving end 204 may also be provided to assist in driving the implant 200 into the selected implant site. The thread 202 defined by the implant 200 may be driven into a pre-formed bore, a tapped bore, an untapped bore, or any predefined void. Further, the implant 200 may be formed in appropriate dimensions, such as a length, thickness, thread height, etc., to achieve selected results. The implant 200 may also be cannulated and have a similar composition and tool engagement to the dual region implant 70, 90, 110 and 130 as illustrated and described above in FIGS. 4-7.

Figure 10:
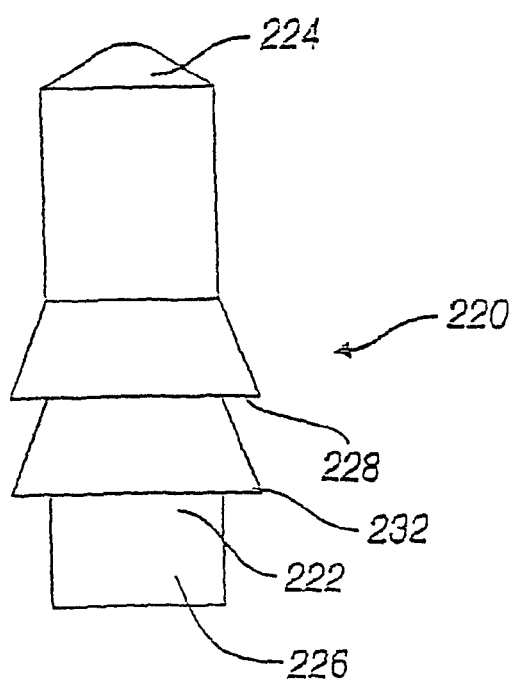
FIG. 10 is an implant according to various embodiments.

With reference to FIG. 10, an implant screw embodiment 220 is illustrated. The implant 220 may include a suture anchor or define a suture anchor to assist in holding a selected suture 222 used in soft tissue repair. For example, the suture 222 may be to reattach a soft tissue region to bone or other soft tissue. In various embodiments, implant 220 may be used as an interference screw in ligament repair or replacements as described herein. The implant 220 may define a shaft or body including a first end 224 and a second end 226. The body of the implant 220 may further have a first engaging or interference portion 228 extending therefore. Further, a second interference portion 230 may also be provided.

The implant 220 may then be driven into the bone of the soft tissue fixation site. The suture 222 is then used to affix the soft tissue to bone. The implant 220 may be generally driven into a bore formed in the portion of the anatomy including a diameter less than a diameter or dimension of the interference portions 228, 230. Therefore, the implant 220 may form an interference fit with a selected portion of the anatomy to hold the suture 222 relative to the selected portion of the anatomy. The implant 220 may also be cannulated and have a similar composition and tool engagement to the dual region implant 70, 90, 110 and 130 as illustrated and described above in FIGS. 4-7.

Method of Manufacturing Implants

Figure 11:
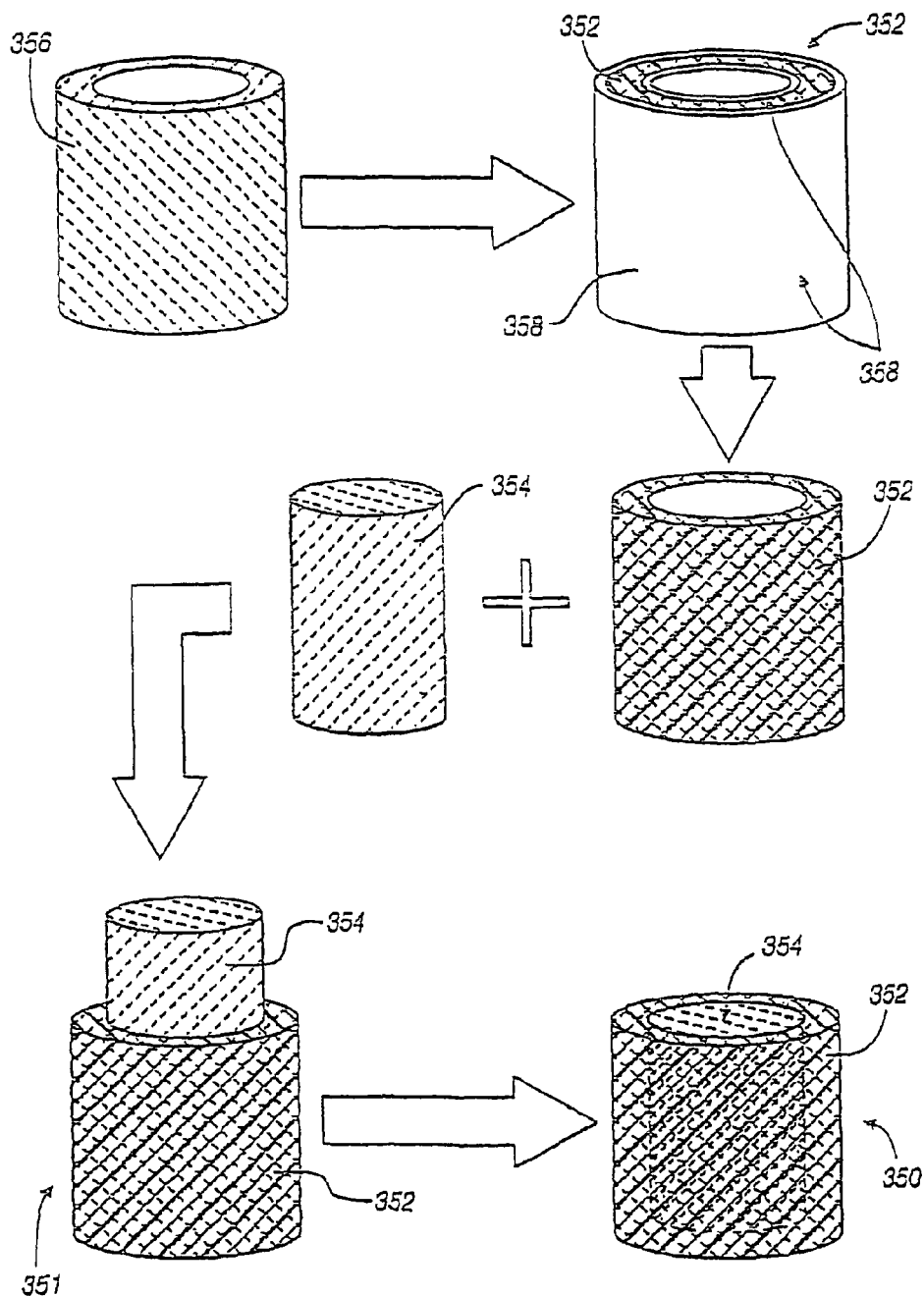
FIG. 11 illustrates a method of forming an implant according to various embodiments.
Figure 12:
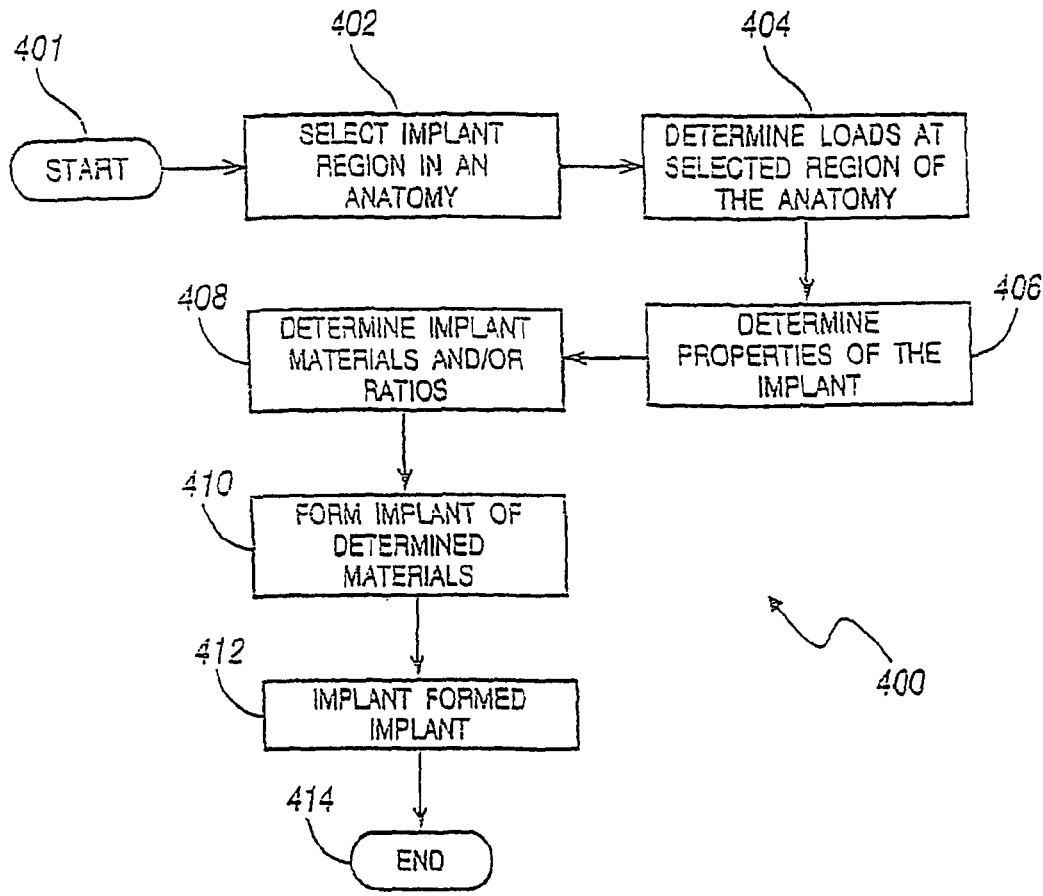
FIG. 12 is a flow chart illustrating a method of selecting material for the forming of an implant according to various embodiments.

With reference to FIG. 11, an implant 350 may be formed according to the illustrated method 351. A blank 356 may be formed of the structure 10. The structure 10 may be any appropriate porous material, such as a polymer matrix, ceramic, or the like. The blank 356 may also be shaped into any appropriate geometry, such as a cylinder.

The blank 356 may then be injected with the second material 21, such as a polymer, as discussed above. This may create polymer portions 358 that extend from a composite 352 that may be similar to the composite 20. The injection may occur by melting the second material 21 and injecting it under pressure into the pores 16 and/or channels defined by the blank 356. The composite 352 may then have the exterior polymer portions 358 removed to include substantially only the composite 352.

A fill material 354 such as, for example, polymer, may then be inserted into the composite 352 form. The fill material 354 may be any appropriate material. For example, the fill material 354 may be substantially similar to the material that formed the blank 356. The two portions, including the fill material 354 and the composite 352, may then be heated to meld the two together to form the implant 350. In the implant 350, the fill material 354 may be formed into the implant 350 and provided complete for a procedure. Thus, implant 350 may be formed to include voids or pre-filled voids. The fill material 354 may serve the same purpose as the graft material discussed above, such as a void filling or support purposes. Nevertheless, the implant 350 may include the fill material 354 and be manufactured with the fill material 354.

With reference to FIG. 11, a flow chart describes a method 400 for forming an implant according to various embodiments. The method 400 may begin at a start block 401. Then a selected implant region is selected in block 402. The implant region may be any appropriate region of the anatomy. For example, a spinal region, a tibial region, a femoral region, a humeral region, or the like may be selected. As discussed above, an implant may be formed for any appropriate portion of the anatomy using the composite 20.

After the implant region is selected in block 402, loads may be determined relative to that the region in block 404. For example, a compressive force, shear force, torsion force, or the like, may be determined at the selected region of the anatomy. For example, it may be determined that about 1500 N to about 3000 N may be experienced in a spinal region. Although other forces may be determined, the forces may depend upon a patient, the region selected, and other considerations.

Also, other forces that the implant may experience can be determined. For example, a torsion stress necessary for implantation may be determined. Thus, not only forces in the selected region of the anatomy, as selected in block 402, but other forces may be determined in block 404. Properties of an implant may then be determined in block 406. For example, after the experienced forces are determined in block 404, the forces that the implant may be required to withstand, for various reasons, can be determined. Therefore, the loads determined in the anatomical region may be different than those determined as a property of the implant in block 406, but they may be related.

Also, a selected resorption time may be a property selected in block 406. For example, a resorption time of the implant may depend upon selected loads in the region of the anatomy or ingrowth rates at the selected regions, or other selected reasons. Thus, the resorption time or profile of the implant may be determined in block 406. In this regard, bond ingrowth in various regions of the body may vary depending on the region, loads encountered and anatomical condition of the area of interest.

Then implant materials may be determined in block 408. The materials selected may be the appropriate material to form the structure 10 or the appropriate second material 21 for the fill of the pores 16. Although, as discussed above, both the structure 10 and the fill for the pores 16 can be polymers or both can be ceramic materials. Also, the implant materials may be selected to achieve the selected properties, such as a strength, strength degradation profile, resorption profile, load-bearing, etc. As also discussed above, the materials selected may be a second material 21 of a selected molecular weight, a certain co-polymer, etc.

Also, the configuration or form of the implant can be determined when determining the implant materials in block 408, or at any appropriate time. As discussed above, the implant may include a composite portion (such as composite 20) and a noncomposite portion (such as second material 21). Therefore, to achieve the determined properties of the implant, such designs may also be determined in block 408.

Then the implant can be formed in block 410. The implant may be formed of the materials determined in block 408 and the configuration determined in block 408. The implant may be formed according to any appropriate method and the formation method may also be chosen depending upon a selected property. For example, the second material 21 may be melted and then injected into the porous structure 10. Nevertheless, any appropriate method may be used to form the implant in block 410.

The implant formed in block 410 may then be implanted in block 412. As discussed above, the implant may be customized by a user prior to implantation or it may be implanted as formed in block 410. Also, a graft material may be used with the implant formed in block 410, also as discussed above. Generally, however, after the implant is formed in block 410, it can be implanted in block 412. Then, generally, the method 400 ends in block 414.

The method 400, however, is merely exemplary and an implant may be formed of the composite 20 according to any appropriate method. The implant formed according to method 400 can include a selected property to achieve selected results after implantation. The selected properties can be achieved by selecting appropriate materials for the composite implant, a selected configuration of the implant, or other appropriate considerations.

Also, regardless of the method chosen, the composite 20 may be used to form an implant that includes a selected strength over a selected period of time, yet can still allow ingrowth of bone. The composite 20 may be formed into an implant where bone may grow into regions that are faster resorbing than other regions. This may be created by including the faster resorbing phase and the slower resorbing phase. The difference in resorption rates may be any appropriate difference, such as about 10% different to about 200% different. Regardless, the slower resorbing phase may be selected for a strength quality to achieve a selected strength degradation profile, while the faster responding phase may be selected based upon the bone regrowth rate of the area of interest. This can assist in bone regrowth and in allowing recovery when a resorption may be selected in a load-bearing area of the anatomy. This may also be used to achieve a selected strength of the implant for a selected period for any appropriate purpose.

As otherwise understood, the method 400 can be used to select materials and properties of the materials for a selected or unique application. The known or determined bone growth rate of a selected region of the anatomy can be used to assist in determining the materials to be used in forming the implant, the ratios of the materials to be used, or the specific properties of the materials to be used. Also, the forces that are experienced in a selected region of the anatomy may be used to select the materials to be used to form an implant. Thus, a higher selected strength may be used to select different materials for forming the implant. Therefore, the method 400 may be used to select materials for an implant, select a structure of an implant, or selected other features of the implant.

Methods of Treatment

The present technology provides methods of using the implants or implantable screws disclosed herein for tissue repair, including ligament repair procedures. The ACL and PCL procedures, for example, may be performed arthroscopically and, generally, involve preparing a bone tunnel through the tibia and adjacent femur, placing a ligament graft extending between the two bone tunnels, and securing each end of the graft within its respective tunnel.

One common method of ACL reconstruction employs the use of bone-tendon-bone ligament grafts bone ligament grafts (harvested from the patella and tibia) where the bone block at each end of the graft is fixed within its respective tunnel by an implantable interference screw secured within each tunnel between the tunnel wall and the adjacent bone block. The interference screw is aligned parallel to the axis of the tunnel and holds the bone block in the tunnel by wedging it against the tunnel wall opposite the interference screw and by engaging the bone block and the adjacent tunnel wall with the interference screw threads. Another common method employs the use of soft tissue grafts (semitendinosus, hamstring, Achilles, quadriceps, etc.) where the ends of the graft are secured by an interference screw similarly interposed between the wall of the bone tunnel and the adjacent soft tissue of the graft.

A widely used technique for the reconstruction of the ACL is known as the Jones procedure. The basic steps in the procedure include harvesting a graft made from a portion of the patellar tendon with attached bone blocks; preparing the graft attachment site by drilling holes in opposing bones of the joint in which the graft will be placed; placing the graft in the graft attachment site; and rigidly fixing the bone blocks in place within the graft site, in the holes or bone tunnels. The interference screws used to fix the graft in place are wedged between the bone block and the wall of the hole into which the bone block fits. Typically, there is very little space between the bone block and the hole in the bone at the fixation site. See, for example, U.S. Pat. Nos. 4,870,957; 4,927,421; 4,950,270; 5,062,843; 5,300,077; 5,931,869; 6,019,797; 6,254,604; 6,264,694; 6,280,472; 6,280,840; 6,354,604; 6,482,232; 6,755,840; 6,905,513; 6,916,321; and 7,033,364.

Figure 13:
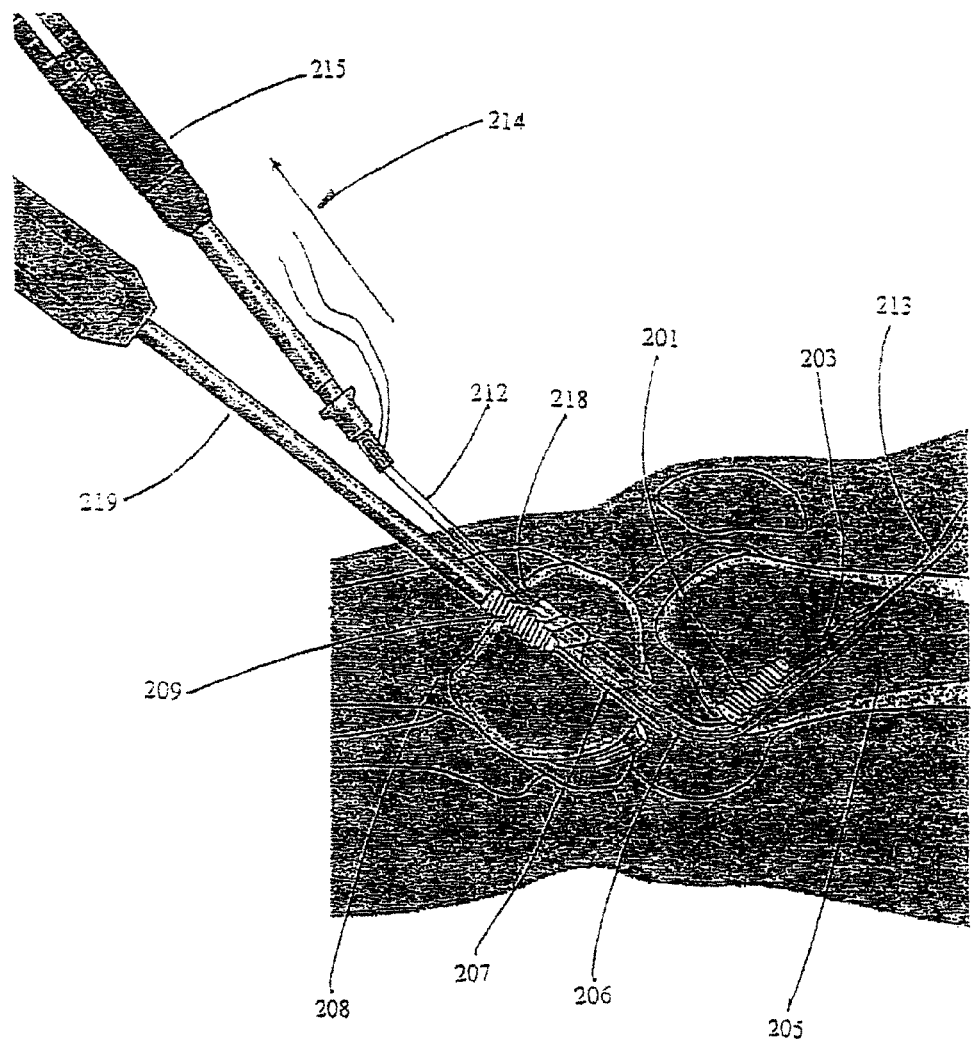
FIG. 13 is a cross-sectional view of an example of attaching an ACL in the tibia employing an implant according to various embodiments.
Figure 14:
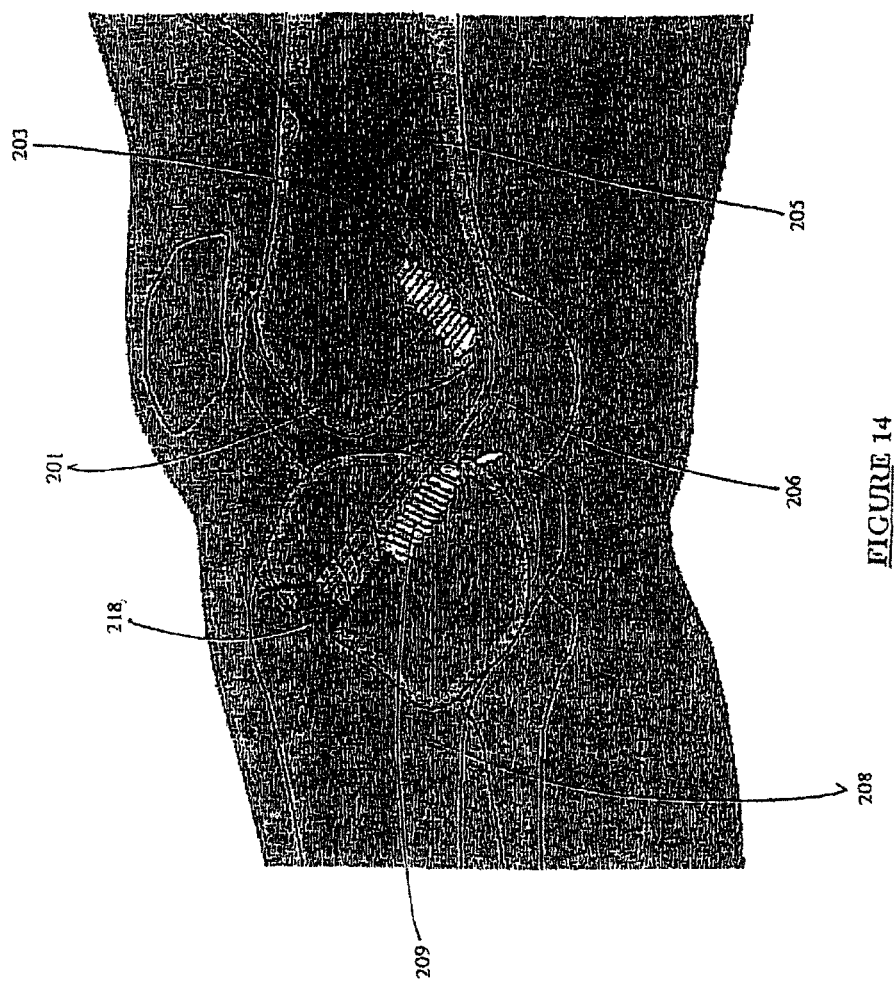
FIG. 14 is a cross-sectional view of an example of a surgically reconstructed ACL employing an implant according to various embodiments.

With reference to FIGS. 13 and 14, a general method for ACL reconstruction is outlined. Substitute ligament 206 may be an audiograph, such as a patellar tendon, a portion of a patellar tendon harvested from a patient, or may be a ligament or a tendon harvested from another part of the patient's body such as from a hamstring, an Achilles tendon, or the fascia lata. In various embodiments, the substitute ligament 206 may be synthetic. A hole or a first tunnel 203 is drilled in the femur 208. A second tunnel 218 is drilled in the tibia 208. The substitute ligament 206 may be bundled and sutures 212, 213 are added at either end using a guide wire in suture 204, the substitute ligament 206 is pulled through the second tunnel 218 and the through the first tunnel 203. Tunnels 203, 218 may be bore using a drill bit and may employ additional tools such as a tubular tunnel guide and a dilation tool, to create a proper hole in a proper position. Tunnels 203, 218 may be started using a pilot tool. Once the substitute ligament 206 has been pulled through the tunnels 203, 218 a first interference screw 201 is driven into first tunnel 203 such that threads of the first interference screw 201 engage in the walls of the first tunnel 203 and substitute ligament 206. The first interference screw 201 is driven using driver 219. After the fixation of the first interference screw 201, such that ligament 206 is secure, tension tool 215 pulls suture 212 with a known force 214. Such known force 214 may be between about 50 N and about 100 N. As force 214 is applied to substitute ligament 206, the second interference screw 209 is driven into the second tunnel 218. The second interference screw 209 may be driven into femur 208 using a guide 207 to ensure that it has been driven into femur 208 correctly. The second interference screw 209 engages the wall of second tunnel 218 and the substitute ligament 206 such that the substitute ligament 206 is affixed and secure within femur 208. In some embodiments, substitute ligament 206 may include bone block at either end of the substitute ligament 206 such that the interference screws (201, 209) engage the bone block and the wall of the tunnel. In various embodiments, interference screws 201, 209 may be any of the interference screws 70, 90, 110, 130, 170, 200, 220 and their equivalents, as described above. In various embodiments, interference screws 201, 209 may be comprise autologous tissue which may include at least one of platelet rich plasma, concentrated bone marrow, and lipoaspirate cells.

In various embodiments, therapeutic agents are used in conjunction with the interference screws 201, 209. In general, therapeutic agents which may be administered in various embodiments include, without limitation, anti-infectives such as antibiotics and antiviral agents; chemotherapeutic agents (i.e. anticancer agents); anti-rejection agents; analgesics and analgesic combinations; anti-inflammatory agents; hormones such as steroids; growth factors, including bone morphogenic proteins (i.e. BMP's 1-7), bone morphogenic-like proteins (i.e. GFD-5, GFD-7 and GFD-8), epidermal growth factor (EGF), fibroblast growth factor (i.e. FGF 1-9), platelet derived growth factor (PDGF), insulin like growth factor (IGF-I and IGF-II), transforming growth factors (i.e. TGF-$\beta$ I-III), vascular endothelial growth factor (VEGF); and other naturally derived or genetically engineered proteins, polysaccharides, glycoproteins, or lipoproteins.

In various embodiments, interference screws 201, 209 may comprise at least one of platelet rich plasma (PRP), concentrated bone marrow aspirate, and lipoaspirate cells. In various embodiments, interference screws 201, 209 may comprise at least one of hematopoietic stem cells, stromal stem cells, mesenchymal stem cells, endothelial progenitor cells, red blood cells, white blood cells, fibroblasts, reticulacytes, adipose cells, or endothelial cells. Any of the above cells, PRP, and/or concentrated bone marrow aspirate may be obtained by using centrifugation methods and an example of such methods is disclosed in U.S. Patent Application Publication No. 2005/0109716. In various embodiments, composite may be soaked in at least one fraction created by centrifugation. The at least one fraction may include at least one of PRP, concentrated bone marrow aspirate, lipoaspirate cells, hematopoietic stem cells, stromal stem cells, mesenchymal stem cells, endothelial progenitor cells, red blood cells, white blood cells, fibroblasts, reticulacytes, adipose cells, endothelial cells, any other autologous tissue and combinations thereof.

According to various embodiments, interference screw 201, 209 comprise concentrated bone marrow aspirate made by a method for concentrating bone marrow aspirate and blood, including collecting bone marrow aspirate and blood from a patient, then loading the bone marrow aspirate and/or blood into a separator that can separate the bone marrow aspirate and/or blood into three or more fractions. The method includes centrifuging the separator containing the bone marrow aspirate and the blood creating a fraction that has a concentrated bone marrow aspirate and/or a concentrated blood component. In various embodiments, such a concentration may be a buffy coat. The method also includes withdrawing the fraction comprising the concentrate or buffy coat.

According to various embodiments, interference screw 201, 209 comprises concentrated bone marrow aspirate and/or blood, or a blood fraction. Such materials may be derived by loading bone marrow aspirate and/or blood into a separator that can separate the bone marrow aspirate and/or blood into three or more fractions. The method also includes centrifuging the separator then withdrawing a fraction comprising at least one of the group consisting of buffy coat, hematopoietic stem cells, stromal stem cells, mesenchymal stem cells, endothelial progenitor cells, red blood cells, white blood cells, fibroblasts, reticulacytes, adipose cells, and endothelial cells, then applying the fraction to an implant according to disclosure, and implanting the implant.

In various embodiments, a kit may include at least one interference screw such as those interferences screws described herein and, more specifically, interference screws 70, 90, 110, 130, 170, 200, 220; and a driver operable to drive the screw into a tunnel in a patient's bone. In various embodiments, the kit of the interference screw comprises a tool engagement area that cooperates with the driver. The total engagement area may have a cross-sectional area of a hexagonal (hex or Allen), a slot, a square, a tapered square (Robertson), an oval, a cruciform shape, a star (Torx®), or a cross (Philips). In various embodiments, the kit further comprises at least one of a drill bit, a dilator, a tibia tunnel guide, a modular guide, a graft prep table, bone coring instrument, a tibial reamer, an imprigment rod, a femoral aimer, an acorn reamer, a washer, a top, a guide wire, a dilator, a pull-through suture, and a pilot hole tool.

The various embodiments and the examples described herein are exemplary and not intended to be limiting in describing the full scope of compositions and methods of this technology. Equivalent changes, modifications, and variations of the various embodiments, materials, compositions, and methods can be made within the scope of the present technology with substantially similar results.

What is claimed is:

1. An implantable interference screw for use in soft tissue repair, the screw comprising:
    a substantially-cylindrical ceramic body having a tapered end, at least a portion of said ceramic body comprising a plurality of interconnected pores;

an instrument interface at the end of said ceramic body opposite to said tapered end, wherein a first volume of a bioresorbable polymer is structurally reinforcing said instrument interface;

a thread starting near said tapered end, and surrounding at least a portion of a surface of said ceramic body; and a second volume of the bioresorbable polymer filling at least a portion of said plurality of interconnected pores.

2. A screw according to claim 1 further comprising a coating covering at least a portion of a surface of said plurality of interconnected pores.

3. A screw according to claim 1 wherein said plurality of pores have a size of from about 350 microns to about 550 microns.

4. A screw according to claim 1 wherein said ceramic body is bioresorbable.

5. A screw according to claim 4 wherein said ceramic body and said bioresorbable polymer are bioresorbable at different rates.

6. A screw according to claim 1 wherein said ceramic body comprises a material selected from the group consisting of calcium phosphate, calcium carbonate, calcium oxide, calcium sulfate, hydroxyapatite, magnesium calcium phosphate, and combinations thereof.

7. A screw according to claim 1 wherein said bioresorbable polymer is selected from the group consisting of aliphatic polyesters, polyorthoesters, polyanhydrides, polycarbonates, polyurethanes, polyamides and polyalkylene oxide, and combinations thereof.

8. A screw according to claim 1 wherein said instrument interface comprises an open area in said interface having a cross-sectional shape selected from the group consisting of a hex, an oval, a slotted square, a tapered square, a cruciform, a cross, and a star.

9. A screw according to claim 1 further comprising at least one of platelet rich plasma, concentrated bone marrow aspirate and lipoaspirate cells.

10. A screw according to claim 9 wherein said at least one of the platelet rich plasma, concentrated bone marrow aspirate, and lipoaspirate cells are isolated by centrifugation.

11. A kit for surgical repair of an ACL, the kit comprising:
a drive tool; and
at least one interference screw comprising,
a bioabsorbable ceramic structure having a plurality of interconnected pores filled with a bioabsorbable polymer,
said interference screw having an elongated threaded body, the elongated threaded body having a proximal end, a distal end, a length, a thread, and a taper, the thread of the interference screw extending substantially along the entire length of the interference screw from said proximal end to said distal end,
the elongated threaded body having a hollowed area in the proximal end operable for engagement of said drive tool, said hollowed area reinforced with said bioabsorbable polymer.

12. A kit according to claim 11 further comprising at least one of a drill bit, a dilator, a tibia tunnel guide, a modular guide, a graft prep table, a bone coring instrument, a tibial reamer, an imprigment rod, a femoral aimer, an acorn reamer, a top, a washer, a guide wire, a dilator, a pull-through suture, and a pilot hole tool.

13. An interference screw comprising a substantially cylindrical ceramic body having a tapered end and a thread starting near said tapered end, the body further comprising:
a bioabsorbable ceramic scaffold having a plurality of interconnecting channels;
a first volume of a bioabsorbable polymer in a majority of said plurality of interconnecting channels; and
a tool engagement region that is reinforced with a second volume of said bioabsorbable polymer.

14. A screw according to claim 13 further comprising an autologous tissue filling a minority of said plurality of interconnecting channels including at least one of platelet rich plasma, concentrated bone marrow aspirate, and lipoaspirate cells.

15. A screw according to claim 13 wherein the tool engagement region is in a hollow area of said body and threads surround the exterior of the body from the tapered end to a substantially flat top, said top having a hole in communication with the hollow area.

16. A screw according to claim 13 wherein said tool engagement region has a cross-sectional area that has a shape selected from the group consisting of a hex, an oval, a slotted square, a tapered square, a cruciform, a cross, and a star.

17. A screw according to claim 13 wherein said interconnecting channels have a size of from about 350 microns to about 550 microns.

18. A screw according to claim 13 wherein said bioabsorbable ceramic scaffold and said bioabsorbable polymer are bioresorbable at different rates.

19. A screw according to claim 13 wherein said bioabsorbable ceramic scaffold and said bioabsorbable polymer are bioresorbable at the same rates.

20. A screw according to claim 13 wherein said bioabsorbable ceramic scaffold comprises a material selected from the group consisting of calcium phosphate, calcium carbonate, calcium oxide, calcium sulfate, hydroxyapatite, magnesium calcium phosphate, and combinations thereof.

21. A screw according to claim 13 wherein said bioabsorbable polymer is selected from the group consisting of aliphatic polyesters, polyorthoesters, polyanhydrides, polycarbonates, polyurethanes, polyamides and polyalkylene oxide, and combinations thereof.

22. A screw according to claim 13 further comprising at least one of platelet rich plasma, concentrated bone marrow aspirate, and lipoaspirate cells.

23. A screw according to claim 22 wherein said at least one of the platelet rich plasma, concentrated bone marrow aspirate, and lipoaspirate cells is isolated by centrifugation.

24. An implantable interference screw system for use in soft tissue repair, the screw comprising:
a substantially-cylindrical ceramic body having a tapered end, at least a portion of said body comprising a plurality of interconnected pores;
an instrument interface at the end of said body opposite to said tapered end with a first bioresorbable polymer structurally reinforcing said instrument interface and contained within a perimeter of said body;
a thread starting near said tapered end, and surrounding at least a portion of a surface of said body; and
a second bioresorbable polymer, other than the first bioresorbable polymer, filling at least a portion of said plurality of interconnected pores.

25. A system according to claim 24, wherein said instrument interface includes a hollowed region in an end of said body operable for engagement of an instrument.

26. A system according to claim 25, further comprising:
said instrument, wherein said instrument engages the reinforced hollowed region through a hole in the end of the body to transfer a torque from the said instrument to said thread.

27. A system according to claim 24, wherein said plurality of pores includes a first sub-plurality of the plurality of pores having a first size range from about 100 microns or less and a second sub-plurality of the plurality of pores having a second size range from about 100 μm or greater;
    wherein the second bioresorbable polymer fills substantially only the second sub-plurality of the plurality of pores.

28. A system according to claim 24, wherein interstitial spaces are between the plurality of interconnected pores within said body.

29. A system according to claim 25 further comprising:
    an autologous tissue filling a minority of said plurality of interconnecting pores;
    wherein said autologous tissue is selected from a group consisting of platelet rich plasma, concentrated bone marrow aspirate, and lipoaspirate cells.

* * * * *